(12) United States Patent
Mototsu et al.

(10) Patent No.: US 7,837,940 B2
(45) Date of Patent: *Nov. 23, 2010

(54) ANALYZER, REAGENT-CONTAINING ASSEMBLY, AND REAGENT SUCTIONING METHOD

(75) Inventors: Kazunori Mototsu, Kobe (JP); Tomoyuki Nishida, Ashiya (JP); Toshihiro Ootani, Kobe (JP); Kazuya Fukuda, Kobe (JP); Motoki Koyama, Kobe (JP)

(73) Assignee: Sysmex Corporation, Kobe-Shi, Hyogo (JP)

( * ) Notice: Subject to any disclaimer, the term of this patent is extended or adjusted under 35 U.S.C. 154(b) by 203 days.

This patent is subject to a terminal disclaimer.

(21) Appl. No.: 11/973,698

(22) Filed: Oct. 10, 2007

(65) Prior Publication Data

US 2008/0095668 A1 Apr. 24, 2008

(30) Foreign Application Priority Data

Oct. 10, 2006 (JP) ............................. 2006-276919

(51) Int. Cl.
*G01N 33/00* (2006.01)
*G01N 35/00* (2006.01)
G01N 33/48 (2006.01)
G01N 35/02 (2006.01)
B01L 3/00 (2006.01)
B01L 9/00 (2006.01)

(52) U.S. Cl. .................. 422/68.1; 422/100; 422/102; 422/104; 422/63; 436/43; 436/47; 436/54

(58) Field of Classification Search .................. 422/102
See application file for complete search history.

(56) References Cited

U.S. PATENT DOCUMENTS

| 2006/0120922 | A1* | 6/2006 | Matsumoto | ................. | 422/64 |
| 2007/0172390 | A1* | 7/2007 | Ootani et al. | ................. | 422/64 |
| 2008/0063570 | A1* | 3/2008 | Fujino et al. | ................. | 422/99 |
| 2008/0085222 | A1* | 4/2008 | Fukuda et al. | ................. | 422/102 |

FOREIGN PATENT DOCUMENTS

| JP | S57-185964 | 11/1982 |
| JP | S64-61667 | 3/1989 |
| JP | H08-94624 | 4/1996 |
| JP | H08-160050 | 6/1996 |
| JP | H10-311835 | 11/1998 |
| JP | 2000-338112 | 12/2000 |
| JP | 2002-48803 | 2/2002 |
| JP | 2006-30170 | 2/2006 |

* cited by examiner

*Primary Examiner*—Jill Warden
*Assistant Examiner*—Jennifer Wecker
(74) *Attorney, Agent, or Firm*—Brinks Hofer Gilson & Lione

(57) ABSTRACT

An analyzer comprising: an assembly holder for holding a reagent-containing assembly comprising an opening and a lid member for opening and closing the opening; an opening-closing section for opening and closing the opening by linearly moving the lid member in a reciprocating manner to substantially horizontal directions; a reagent suctioning section for suctioning reagent by inserting a pipette into the reagent-containing assembly through the opening; and an analyzing section for analyzing an analyzing specimen comprising a sample and the reagent is disclosed. A reagent-containing assembly and reagent suctioning method are also disclosed.

20 Claims, 22 Drawing Sheets

ANALYZER, REAGENT-CONTAINING ASSEMBLY, AND REAGENT SUCTIONING METHOD

RELATED APPLICATIONS

This application claims priority under 35 U.S.C. §119 to Japanese Patent Application No. 2006-276919 filed Oct. 10, 2006, the entire content of which is hereby incorporated by reference.

FIELD OF THE INVENTION

The present invention relates to analyzers, reagent-containing assemblies, and reagent suctioning methods, in particular, to an analyzer with an opening-closing section for opening and closing the opening, a reagent-containing assembly with a lid member for opening and closing an opening, and a reagent suctioning method for suctioning reagent from the reagent-containing assembly.

BACKGROUND

An analyzer capable of automatically opening and closing a lid of a reagent container mounted on a reagent table is known (see e.g., Japanese Laid-Open Utility-Model Publication No. 57-185964, Japanese Laid-Open Patent Publication No. 8-160050, Japanese Laid-Open Patent Publication No. 10-311835, Japanese Laid-Open Patent Publication No. S64-61667, Japanese Laid-Open Patent Publication No. 8-94624, Japanese Laid-Open Patent Publication No. 2000-338112, and Japanese Laid-Open Patent Publication No. 2006-30170).

The analyzer disclosed in Japanese Laid-Open Utility-Model Publication No. 57-185964, for example, has reagent containers mounted on a container shelf, and includes an opening/closing means for opening/closing the opening of the reagent container by rotatably moving the inner lid of the reagent container in a horizontal direction by rotating the container shelf. According to such analyzer, the opening of the reagent container is opened only when suctioning the reagent and the opening is sealed in other times.

However, in the analyzer disclosed in Japanese Laid-Open Utility-Model Publication No. 57-185964, a shaft acting as center of rotation of the inner lid and a spring for sealing the opening by being pushed by a pushing member must be arranged in the reagent container, and thus the structure of the lid is complicating. Some reagent containers are disposable, but if the structure of such disposable reagent container is complex, the cost required for examination increases. If the lid is reusable, replacement of reagent becomes troublesome. Furthermore, lid having complex structure and a lid opening/closing mechanism having complex structure are required in analyzers disclosed in references other than Japanese Laid-Open Utility-Model Publication No. 57-185964.

BRIEF SUMMARY

The scope of the present invention is defined solely by the appended claims, and is not affected to any degree by the statements within this summary.

A first aspect of the present invention is an analyzer comprising: an assembly holder for holding a reagent-containing assembly comprising an opening and a lid member for opening and closing the opening; an opening-closing section for opening and closing the opening by linearly moving the lid member in a reciprocating manner to substantially horizontal directions; a reagent suctioning section for suctioning reagent by inserting a pipette into the reagent-containing assembly through the opening; and an analyzing section for analyzing an analyzing specimen comprising a sample and the reagent.

A second aspect of the present invention is a reagent-containing assembly comprising: an opening; and a lid member for opening and closing the opening by linearly moving in a reciprocating manner to substantially horizontal directions; wherein a surface including an edge of the opening is inclined from a horizontal surface; the lid member comprises a closing surface having an inclination of substantially the same as the inclination of the surface including the edge of the opening; and the closing surface closes the opening by linearly moves to one of the substantially horizontal directions, wherein the direction is a direction from the lower side to the higher side of the closing surface.

A third aspect of the present invention is a reagent suctioning method for suctioning reagent contained in a reagent-containing assembly comprising an opening and a lid member for opening and closing the opening by linearly moving in a reciprocating manner in substantially horizontal directions; the method comprising the steps of: opening the opening by linearly moving the lid member in a first substantially horizontal direction; suctioning the reagent contained in the reagent-containing assembly through the opened opening; and closing the opening by linearly moving the lid member in a second substantially horizontal direction opposite the first direction.

DETAILED DESCRIPTION OF THE PREFERRED EMBODIMENTS

The preferred embodiments of the present invention are described hereinafter with reference to the drawings.

First, an overall configuration of an immune analyzer 1 according to one embodiment of the present invention will be described with reference to FIGS. 1 to 6.

The immune analyzer 1 according to one embodiment of the present invention is an apparatus for carrying out examinations on various items such as hepatitis B, hepatitis C, tumor marker, and thyroid hormone using samples such as blood. In the immune analyzer 1, magnetic particles (R2 reagent) are bonded to a trapped antibody (R1 reagent) bonded to an antigen contained in a sample such as blood, which is the measuring object, and thereafter, the bound antigen, trapped antibody, and magnetic particles are attracted to a magnet (not shown) of a BF (Bound Free) separator 14 (see FIGS. 1 and 2) to remove the R1 reagent containing non-reactive (free) trapped body. A labeled antibody (R3 reagent) is bonded to the antigen bound with magnetic particles, and thereafter, the bound magnetic particles, antigen, and labeled antibody are attracted to a magnet of a BF separator 14 to remove a R3 reagent containing non-reactive (free) labeled antibody. Furthermore, a light emitting substrate (R5 reagent) that emits light in the reaction process with the labeled antibody is added, and a light emitting amount generated through the reaction of the labeled antibody and the light emitting substrate is measured. After such processes, the antigen or the antibody contained in the sample that bonds with the labeled antibody is quantitatively measured.

Figure 1:
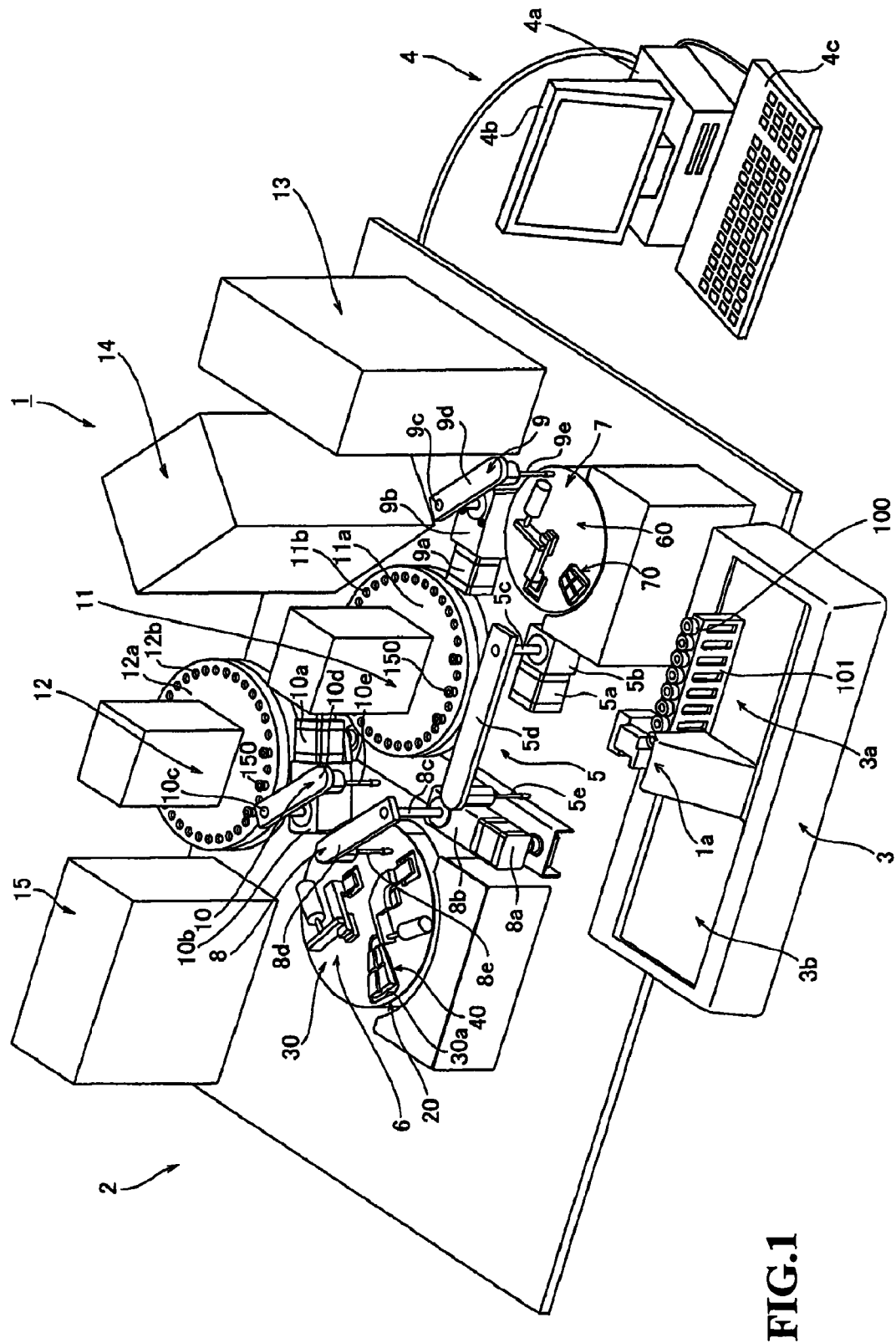
FIG. 1 is a perspective view showing an overall configuration of an immune analyzer according to one embodiment of the present invention.
Figure 2:
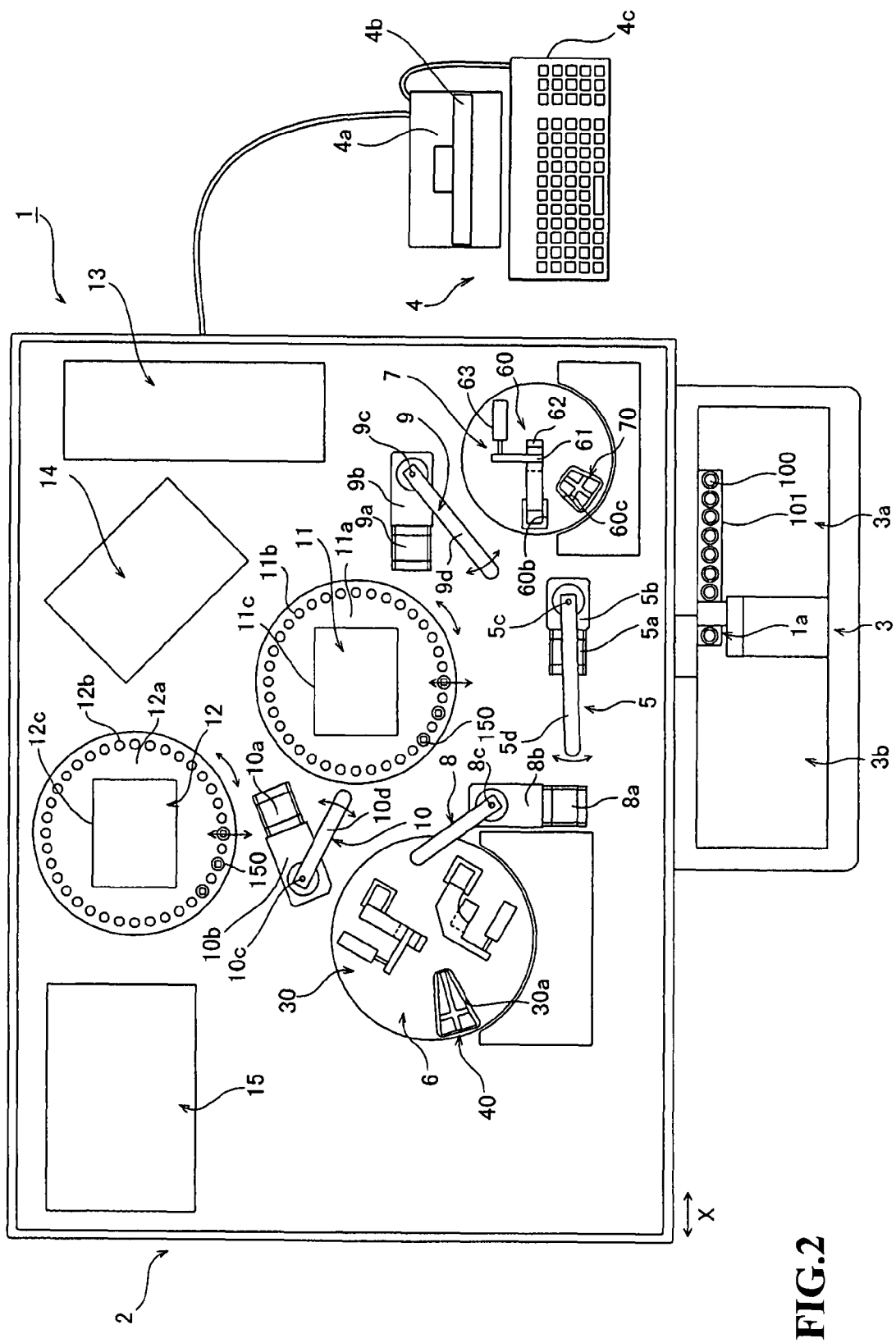
FIG. 2 is a plan view of the immune analyzer shown in FIG. 1.
Figure 3:
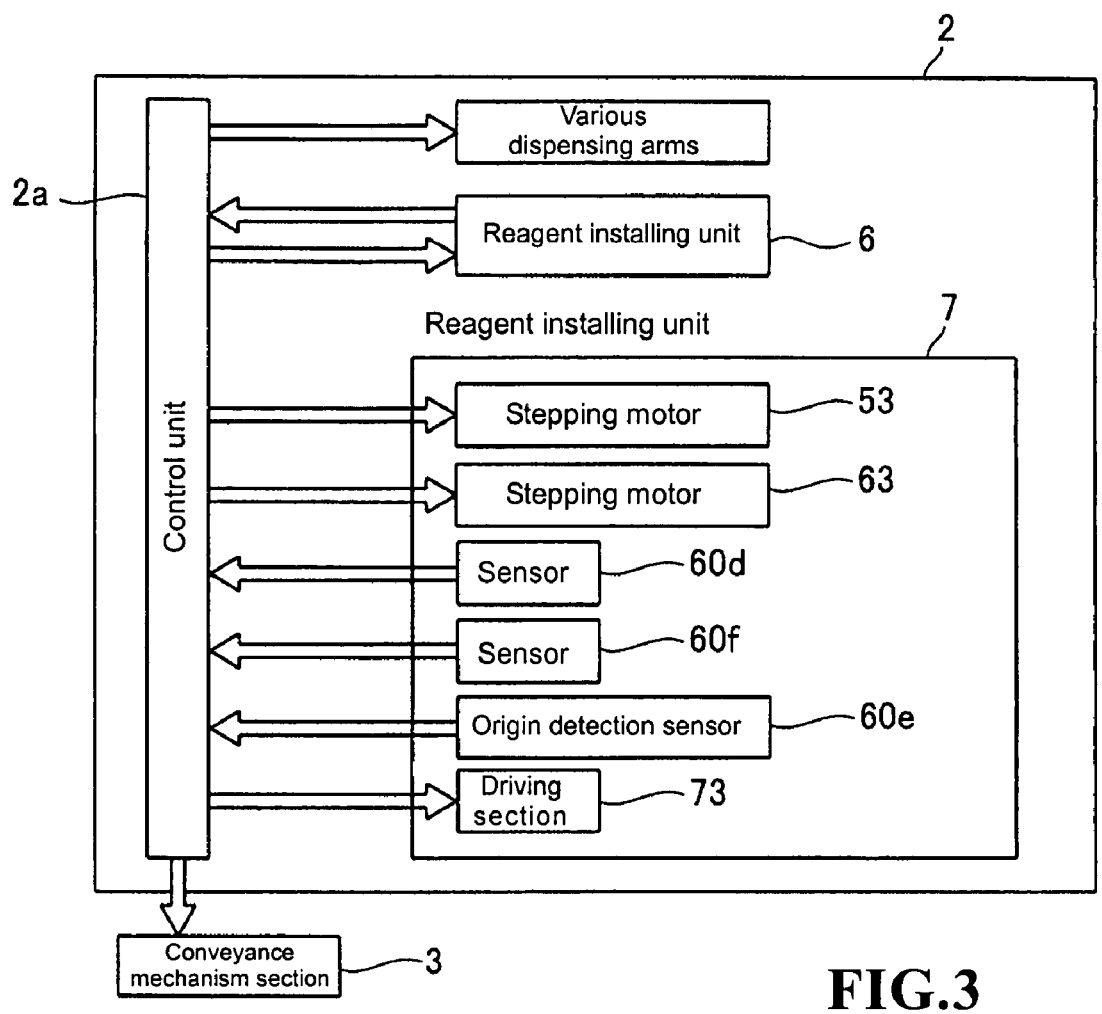
FIG. 3 is a block diagram including a control unit of a measurement mechanism section of the immune analyzer according to one embodiment of the present invention.

As shown in FIGS. 1 and 2, the immune analyzer 1 includes a measurement mechanism section 2, a sample conveyance section (sampler) 3 arranged on the front surface side of the measurement mechanism section 2, and a control device 4 including PC (personal computer) electrically connected to the measurement mechanism section 2. The measurement mechanism section 2 is configured by a sample dispensing arm 5, reagent installing units 6 and 7, reagent dispensing arms 8, 9, and 10, a primary reaction unit 11 and a secondary reaction unit 12, a cuvette supplying unit 13, a BF separator 14, and a detector 15. As shown in FIG. 3, each mechanism (various dispensing arms, reagent installing unit 6, and reagent installing unit 7, and the like) in the measurement mechanism section 2 are controlled by a control unit 2a arranged in the measurement mechanism section 2. Specifically, the control unit 2a receives signals of various sensors (sensors 60d, 60f, and origin detection sensor 60e, and the like) arranged in the reagent installing unit 7, and controls the drive of various driving sources (stepping motors 53, 63, and motor 73, and the like) arranged in the reagent installing unit 7. The conveyance mechanism section 3 is also controlled by the control unit 2a. The various dispensing arms, various sensors, and various driving sources will be described in detail below.

Figure 4:
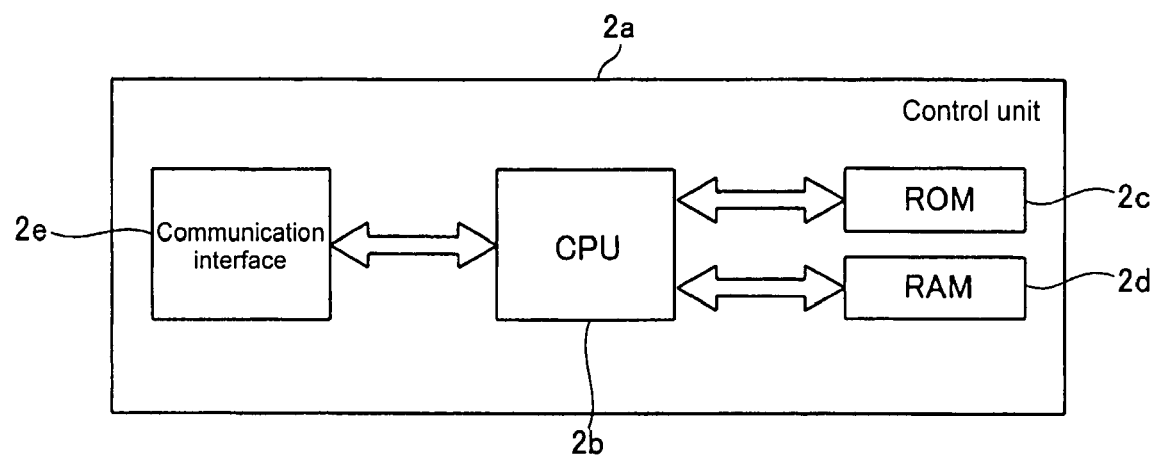
FIG. 4 is a block diagram showing a configuration of the control unit of the measurement mechanism section shown in FIG. 3.

As shown in FIG. 4, the control unit 2a is mainly configured by a CPU 2b, a ROM 2c, a RAM 2d, and a communication interface 2e.

The CPU 2b executes computer programs stored in the ROM 2c and the computer programs read by the RAM 2d. The ROM 2c stores computer programs executed by the CPU 2b, data used in executing the computer program, and the like. The RAM 2d is used to read out the computer program stored in the ROM 2c. In executing the computer program, the RAM 2d is used as a work region of the CPU 2b.

The communication interface 2e is connected to the control device 4, and transmits optical information (data of received light amount generated by reaction of the labeled antibody and light emitting substrate) of the sample to the control device 4, and receives signals from the control unit 4a of the control device 4. The communication interface 2e has a function of transmitting a command from the CPU 2b for driving each unit of the conveyance mechanism section 3 and the measurement mechanism section 2.

As shown in FIGS. 1 and 2, the sample conveyance section 3 is configured to convey a rack 101 mounted with a plurality of test tubes 100 accommodating the sample to a position corresponding to a suction position 1a at where the sample dispensing arm 5 suctions the sample. The sample conveyance section 3 includes a rack set part 3a for setting the rack 101 in which the test tubes 100 accommodating non-processed sample are mounted, and a rack storing part 3b for storing the rack 101 in which the test tubes 100 accommodating the dispensing processed sample are mounted. The test tube 100 accommodating the non-processed sample is conveyed to a position corresponding to the suction position 1a of the sample dispensing arm 5, so that the sample dispensing arm 5 suctions the sample such as blood in the test tube 100, and thereafter, the rack 101 mounted with the test tube 100 is stored in the rack storing part 3b.

The control device 4 (FIG. 1) consists of a personal computer (PC), and includes a control unit 4a including CPU, ROM, RAM, a display unit 4b and a keyboard 4c. The display unit 4b is arranged to display result of analysis obtained by analyzing data of digital signals transmitted from a detector 15.

Figure 5:
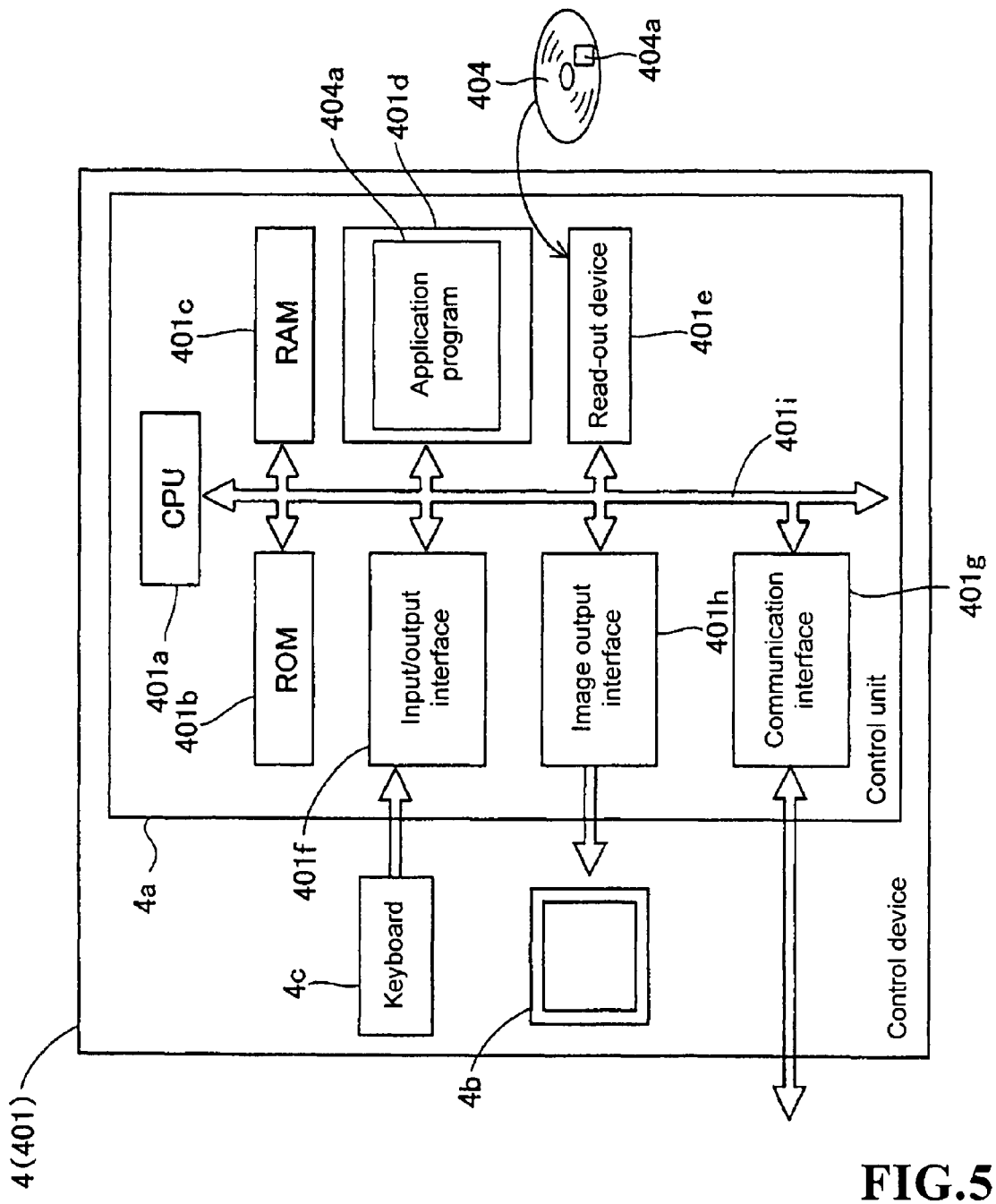
FIG. 5 is a block diagram showing a control device of the immune analyzer according to one embodiment of the present invention.

The configuration of the control device 4 will now be described. As shown in FIG. 5, the control device 4 is configured by a computer 401 mainly consisting of the control unit 4a, the display unit 4b, and the keyboard 4c. The control unit 4a is mainly configured by a CPU 401a, a ROM 401b, a RAM 401c, a hard disc 401d, a read-out device 401e, an input/output interface 401f, a communication interface 401g, and an image output interface 401h. The CPU 401a, the ROM 401b, the RAM 401c, the hard disc 401d, the read-out device 401e, the input/output interface 401f, the communication interface 401g, and the image output interface 401h are connected by a bus 401i.

The CPU 401a executes computer programs stored in the ROM 401b and the computer programs loaded in the RAM 401c. The computer 401 serves as the control device 4 when the CPU 401a executes the application program 404a, as hereinafter described.

The ROM 401b is configured by mask ROM, PROM, EPROM, EEPROM, and the like, and is recorded with computer programs to be executed by the CPU 401a, data used for the same, and the like.

The RAM 401c is configured by SRAM, DRAM, and the like. The RAM 401c is used to read out the computer programs recorded on the ROM 401b and the hard disc 401d. The RAM 401c is used as a work region of the CPU 401a when executing the computer programs.

The hard disc 401d is installed with various computer programs to be executed by the CPU 401a such as operating system and application program, as well as data used in executing the computer program. The immune analysis application program 404a according to the present embodiment is also installed in the hard disc 401d.

The read-out device 401e is configured by flexible disc drive, CD-ROM drive, DVD-ROM drive, and the like, and is able to read out computer programs and data recorded on a portable recording medium 404. The immune analysis application program 404a is stored in the portable recording medium 404, where the computer 401 reads out the application program 404a from the portable recording medium 404, and installs the application program 404a to the hard disc 401d.

The application program 404a is not only provided by the portable recording medium 404, but also provided through communication line (wired or wireless) from external devices communicably connected with the computer 401 through the communication line. For instance, the application program 404a may be stored in the hard disc of the server computer on the Internet, so that the computer 401 can access the server computer to download the application program 404a and install the application program 404a to the hard disc 401d.

Operating system providing graphical user interface environment such as Windows (registered trademark) manufactured and sold by US Microsoft Co. is installed in the hard disc 401d. In the following description, the application program 404a according to the present embodiment is assumed to operate on the operating system.

The output interface 401f is configured by serial interface such as USB, IEEE1394, RS-232C; parallel interface such as SCSI, IDE, IEEE1284; analog interface such as D/A converter, A/D converter, and the like. The keyboard 4c is connected to the input/output interface 401f, so that the user can input data to the computer 401 using the keyboard 4c.

The communication interface 401g is, for example, Ethernet (registered trademark) interface. The computer 401 transmits and receives data with the measurement mechanism section 2 using a predetermined communication protocol by means of the communication interface 401g.

The image output interface 401h is connected to the display unit 4b configured by LCD, CRT, or the like, and is configured to output an image signal corresponding to the image data provided from the CPU 401a to the display unit 4b. The display unit 4b displays the image (screen) according to the input image signal.

The immune analysis application program 404a installed in the hard disc 401d of the control unit 4a measures the amount of antigen or antibody in the measurement specimen using the received light amount (data of digital signal) of the measurement specimen transmitted from the detector 15 of the measurement mechanism section 2.

The sample dispensing arm 5 (see FIGS. 1 and 2) has a function of dispensing the sample in the test tube 100 conveyed to the suction position 1a by the sample conveyance section 3 into a cuvette 150 held by a holder 11b of a rotatable table 11a of the primary reaction unit 11 to be hereinafter described. As shown in FIGS. 1 and 2, the sample dispensing arm 5 includes a motor 5a, a drive transmitting part 5b connected to the motor 5a, and an arm 5d attached to the drive transmitting part 5b by way of a shaft 5c. The drive transmitting part 5b is configured to turn the arm 5d with the shaft 5c as the center by the driving force from the motor 5a, and move the arm in the up and down direction (Z direction). A pipette 5e for suctioning and discharging the sample is arranged at the distal end of the arm 5d.

The reagent installing unit 6 (see FIGS. 1 and 2) is arranged to install the reagent-containing assembly for holding a reagent container in which an R1 reagent containing trapped antibody is accommodated and a reagent container in which a R3 reagent containing labeled antibody is accommodated. As shown in FIG. 1, the reagent installing unit 6 includes a reagent holder 20 for holding the reagent-containing assembly, a lid 30 attached to the reagent holder 20, and a raising and lowering unit 40 for replacing the reagent-containing assembly in the reagent holder 20 through a hole 30a formed in the lid 30.

The reagent installing unit 7 (see FIGS. 1 and 2) is arranged to install a reagent-containing assembly 300 (see FIG. 6) for holding a reagent container in which a R2 reagent containing magnetic particles is accommodated. The configuration of the reagent installing unit 7 will be hereinafter described in detail.

The reagent dispensing arm 8 (see FIGS. 1 and 2) has a function of suctioning the R1 reagent in the reagent-containing assembly installed in the reagent installing unit 6 and dispensing the suctioned R1 reagent into the cuvette 150 dispensed with the sample of the primary reaction unit 11. The reagent dispensing arm 8 includes a motor 8a, a drive transmitting part 8b connected to the motor 8a, and an arm 8d attached to the drive transmitting part 8b by way of a shaft 8c. The drive transmitting part 8b is configured to turn the arm 8d with the shaft 8c as the center by the driving force from the motor 8a, and move the arm in the up and down direction. A pipette 8e (see FIG. 1) for suctioning and discharging the R1 reagent in the reagent-containing assembly is arranged at the distal end of the arm 8d. That is, the pipette 8e is configured to suction the R1 reagent in the reagent-containing assembly installed in the reagent installing unit 6, and thereafter, dispense the suctioned R1 reagent into the cuvette 150 dispensed with the sample of the primary reaction unit 11.

The reagent dispensing arm 9 (see FIGS. 1 and 2) has a function of dispensing the R2 reagent in the reagent-containing assembly 300 installed in the reagent installing unit 7 into the cuvette 150 dispensed with the sample and the R1 reagent of the primary reaction unit 11. The reagent dispensing arm 9 includes a motor 9a, a drive transmitting part 9b connected to the motor 9a, and an arm 9d attached to the drive transmitting part 9b by way of a shaft 9c. The drive transmitting part 9b is configured to turn the arm 9d with the shaft 9c as the center by the driving force from the motor 9a, and move the arm in the up and down direction. A pipette 9e (see FIG. 1) for suctioning and discharging the R2 reagent in the reagent-containing assembly 300 is arranged at the distal end of the arm 9d. Thus, the pipette 9e is configured to suction the R2 reagent in the reagent-containing assembly 300 installed in the reagent installing unit 7, and thereafter, dispense the suctioned R2 reagent into the cuvette 150 dispensed with the sample and the R1 reagent of the primary reaction unit 11.

The reagent dispensing arm 10 (see FIGS. 1 and 2) has a function of suctioning the R3 reagent in the reagent-containing assembly installed in the reagent installing unit 6, and dispensing the suctioned R3 reagent into the cuvette 150 dispensed with the sample, the R1 reagent, and the R2 reagent of the secondary reaction unit 12. The reagent dispensing arm 10 includes a motor 10a, a drive transmitting part 10b connected to the motor 10a, and an arm 10d attached to the drive transmitting part 10b by way of a shaft 10c. The drive transmitting part 10b is configured to turn the arm 10d with the shaft 10c as the center by the driving force from the motor 10a, and move the arm in the up and down direction. A pipette 10e (see FIG. 1) for suctioning and discharging the R3 reagent in the reagent-containing assembly is arranged at the distal end of the arm 10d. That is, the pipette 10e is configured to suction the R3 reagent in the reagent-containing assembly installed in the reagent installing unit 6, and thereafter, dispense the suctioned R3 reagent into the cuvette 150 dispensed with the sample, the R1 reagent, and the R2 reagent of the secondary reaction unit 12.

As shown in FIGS. 1 and 2, the primary reaction unit 11 is arranged to rotatably transfer the cuvette 150 held by the holder 11b of the rotatable table 11a by a predetermined angle for every predetermined period (18 seconds in the present embodiment), and to stir the sample, the R1 reagent, and the R2 reagent in the cuvette 150. That is, the primary reaction unit 11 is arranged to react the R2 reagent containing magnetic particles and the antigen in the sample in the cuvette 150. The primary reaction unit 11 is configured by a rotatable table 11a for conveying the cuvette 150 accommodating the sample, the R1 reagent, and the R2 reagent in the rotating direction, and a container conveying part 11c for stirring the sample, R1 reagent, and R2 reagent in the cuvette 150 and conveying the cuvette 150 accommodating the stirred sample, R1 reagent and R2 reagent to the BF separator 14 (see FIGS. 1 and 2) to be hereinafter described.

The rotatable table 11a is configured so as to rotatably transfer the cuvette 150 held in the holder 11b by a predetermined angle every 18 seconds. Thus, various devices (sample dispensing arm 5, reagent dispensing arms 8 and 9 etc.) of the immune analyzer 1 are controlled so as to operate on the cuvette 150 at the predetermined transferred position at a timing the cuvette is transferred to the predetermined position by the rotatable table 11a.

The container conveying part 11c is rotatably arranged at the central portion of the rotatable table 11a. The container conveying part 11c has a function of gripping the cuvette 150 held in the holder 11b of the rotatable table 11a and stirring the sample in the cuvette 150. Furthermore, the container conveying part 11c has a function of transferring the cuvette 150 accommodating the specimen obtained by stirring and incubating the sample, the R1 reagent and the R2 reagent to the BF separator 14 (see FIGS. 1 and 2).

The secondary reaction unit 12 (see FIGS. 1 and 2) has a configuration similar to the primary reaction unit 11, and is arranged to rotatably transfer the cuvette 150 held by the holder 12b of the rotatable table 12a by a predetermined angle for every predetermined period (18 seconds in the present embodiment), and to stir the sample, the R1 reagent, the R2 reagent, the R3 reagent, and the R5 reagent in the cuvette 150. That is, the secondary reaction unit 12 is arranged to react the R3 reagent containing labeled antibody and the antigen in the sample in the cuvette 150, and to react the R5 reagent containing light emitting substrates and the labeled antibody of the R3 reagent. The R5 reagent is dispensed into the cuvette 150 accommodating the sample, the R1 reagent, the R2 reagent, and the R3 reagent of the secondary reaction unit 12 by a R5 reagent dispensing arm (not shown) arranged near the secondary reaction unit 12. The secondary reaction unit 12 is configured by a rotatable table 12a for conveying the cuvette 150 accommodating the sample, the R1 reagent, the R2 reagent, the R3 reagent, and the R5 reagent in the rotating direction, and a container conveying part 12c for stirring the sample, the R1 reagent, the R2 reagent, R3 reagent, and the R5 reagent in the cuvette 150 and conveying the cuvette 150 accommodating the stirred sample etc. to the BF separator 14. The container conveying part 12c has a function of again conveying the cuvette 150 processed by the BF separator 14 to the holder 12b of the rotatable table 12. The detailed structure of the secondary reaction unit 12 is similar to the primary reaction unit 11, and thus the description thereof will be omitted.

The cuvette supplying unit 13 (see FIGS. 1 and 2) is configured to sequentially supply a plurality of cuvettes 150 to the holder 11b of the rotatable table 11a of the primary reaction unit 11.

The BF separator 14 has a function of separating the non-reacting R1 reagent (unnecessary component) and the magnetic particles from the specimen in the cuvette 150 conveyed by the container conveying part 11c of the primary reaction unit 11, and a function of separating the non-reacting R3 reagent (unnecessary component) and the magnetic particles from the specimen in the cuvette 150 (see FIG. 1) conveyed by the container conveying part 12c of the secondary reaction unit 12.

The detector 15 (see FIGS. 1 and 2) is arranged to measure the amount of antigen contained in a sample by acquiring the light generated in the reaction process of the labeled antibody bound to the antigen of the sample performed with a predetermined process and the light emitting substrate with a photo multiplier tube.

The structure of the reagent installing unit 7 of the immune analyzer 1 and the reagent-containing assembly 300 installed in the reagent installing unit 7 according to one embodiment of the present invention will now be described with reference to FIGS. 6 to 17.

Figure 6:
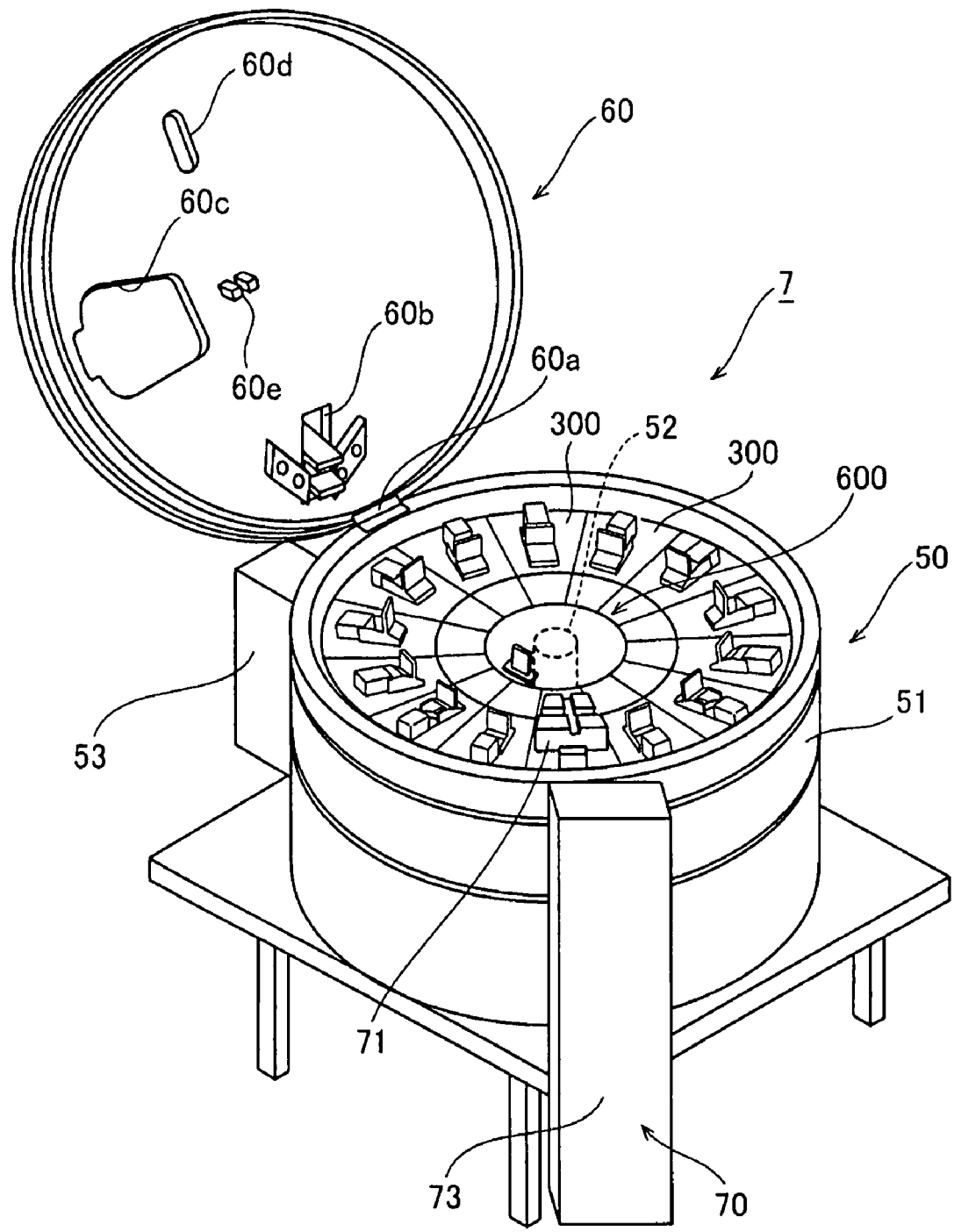
FIG. 6 is a perspective view showing an overall configuration of a reagent installing unit shown in FIG. 1.

As shown in FIG. 6, the reagent installing unit 7 includes a reagent holder 50 of cylindrical shape for holding the reagent-containing assembly 300 in a circular ring shape, a lid 60 attached to the reagent holder 50 in an openable and closable manner, and a raising and lowering unit 70 attached to the side surface (outer wall part 51) of the cylindrical reagent holder 50. A Peltier element (not shown) is also attached at the bottom of the reagent installing unit 7, and the inside of the reagent installing unit 7 is maintained at about 15° C.

Figure 7:
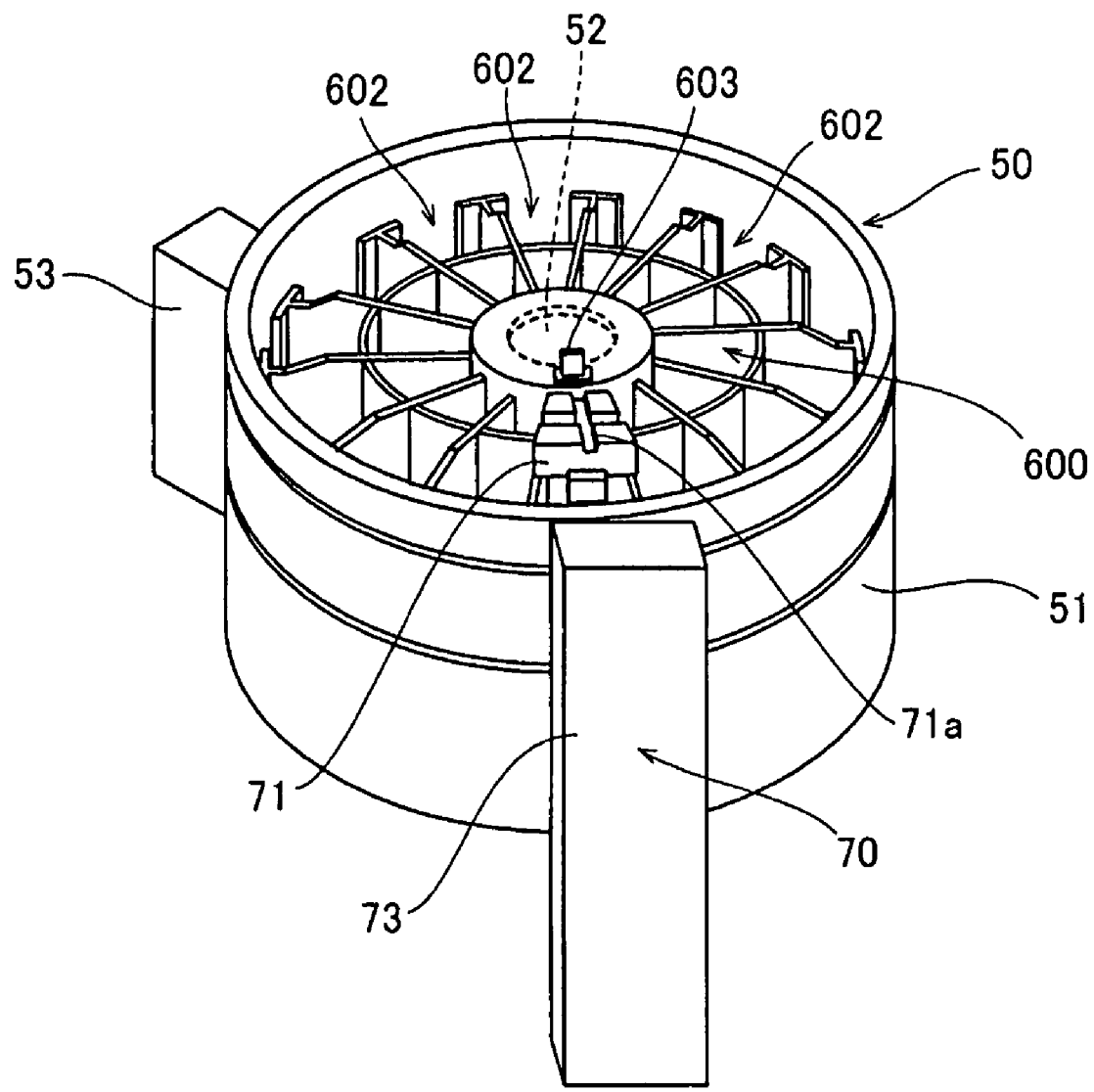
FIG. 7 is a perspective view showing a reagent holder of the reagent installing unit shown in FIG. 6.
Figure 8:
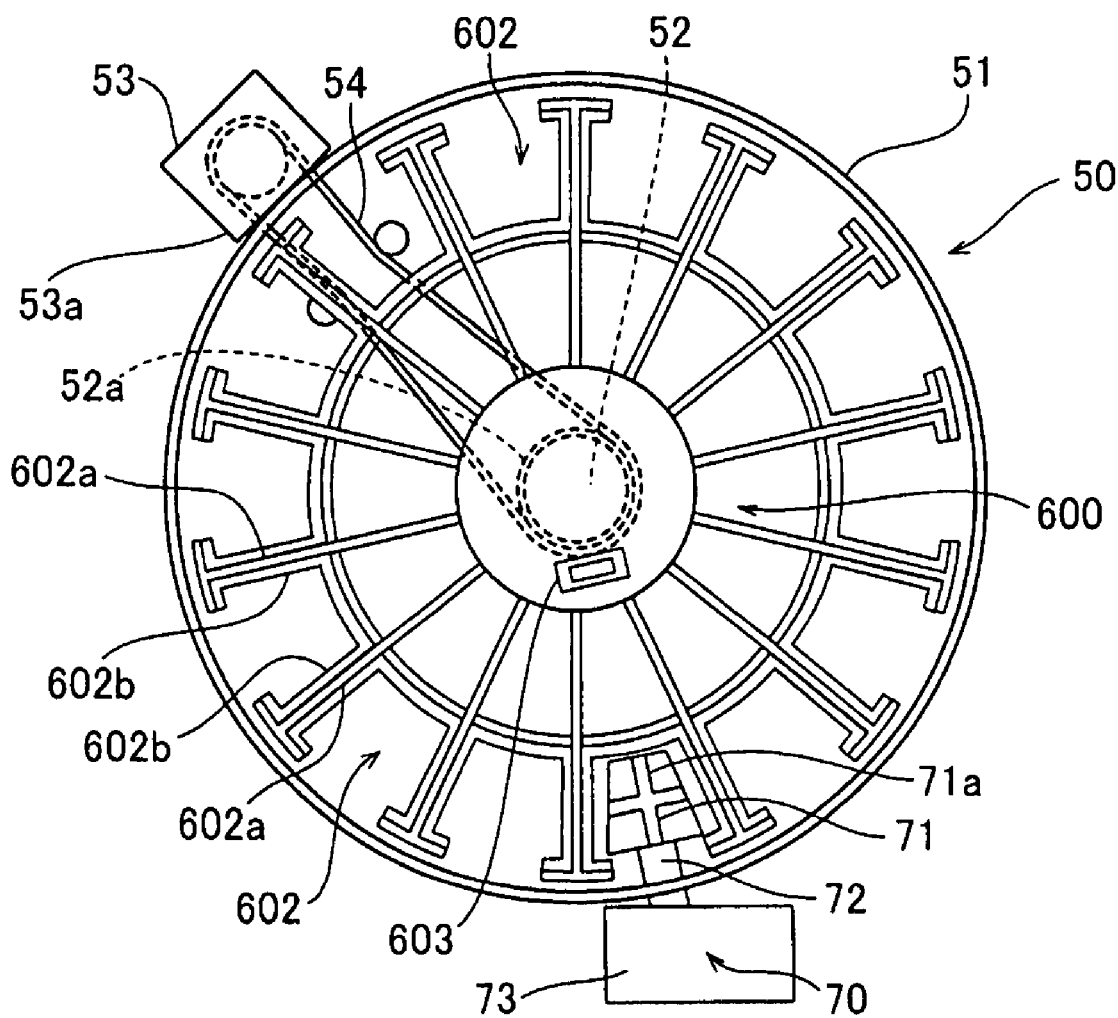
FIG. 8 is a plan view of the reagent holder of the reagent installing unit shown in FIG. 6.

As shown in FIGS. 7 and 8, the reagent holder 50 includes a cylindrical outer wall part 51, a rotatable rotation shaft 52 arranged at the center, a stepping motor 53 for rotating the rotation shaft 52, and a belt 54 for transmitting the driving force of the stepping motor 53 to the rotation shaft 52 (see FIG. 8). A heat insulating material (not shown) is attached over the entire surface on the inner surface of the outer wall part 51, so that the temperature inside the reagent holder 50 is maintained at low temperature (about 15° C.). As shown in FIG. 8, the driving force of the stepping motor 53 is transmitted to the rotation shaft 52 via the belt 54 by a pulley 53a that rotates by the stepping motor 53 and a pulley 52a coaxially fixed to the rotation shaft 52.

Figure 9:
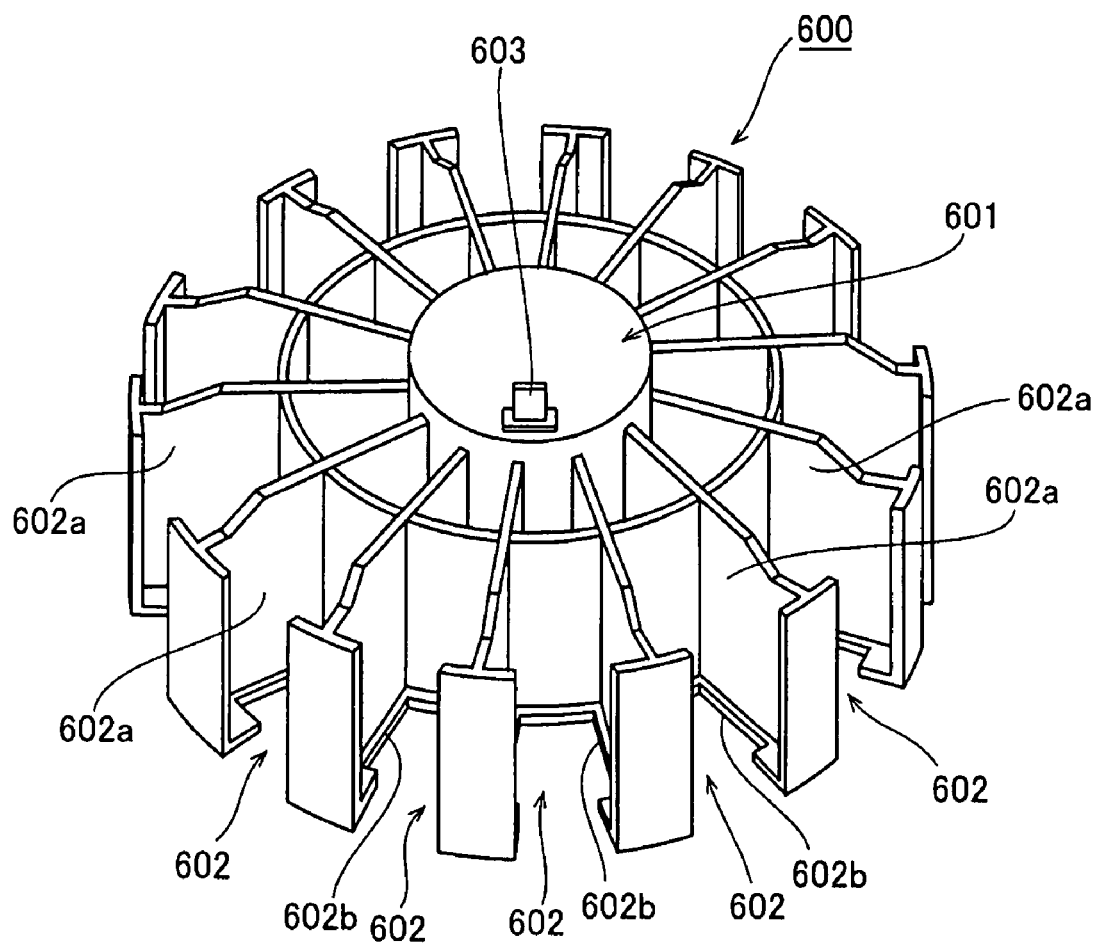
FIG. 9 is a perspective view showing a rack for holding the reagent-containing assembly used in the immune analyzer according to one embodiment of the present invention.

As shown in FIG. 6, a rack 600 for holding a plurality of reagent-containing assemblies 300 in a circular ring form is fixedly attached to the rotation shaft 52. The rack 600 holding the reagent-containing assemblies 300 rotates when the rotation shaft 52 is rotated with the reagent-containing assemblies 300 held in the rack 600, and thus the reagent-containing assembly 300 holding the reagent to be suctioned can be moved to below a hole 60b of the lid 60 to be hereinafter described. As shown in FIG. 9, the rack 600 includes an inserting part 601, formed at the center of the rack 600, to which the rotation shaft 52 is inserted; a plurality of holders 602, formed in a circular ring form with the inserting part 601 as the center, for holding the reagent-containing assembly 300, and an origin detection strip 603 arranged so as to project above the inserting part 601. The holder 602 is configured by a partition plate 602a and a supporting part 602b. The partition plate 602a is arranged in plurals at a predetermined angular interval so as to radially extend from the inserting part 601. The supporting part 602b is arranged at the lower part of the portions facing each other of the partition plates 602a and at the lower part of the inserting part 601 so as to project to the inner side. Each reagent-containing assembly 300 is arranged such that the peripheral edge of the bottom 326 (see FIG. 14) is supported by the supporting part 602b in a space defined by a pair of partition plates 602a. Furthermore, the mounting platform 71 of the raising and lowering unit 70 for raising and lowering the reagent-containing assembly 300 can be raised and lowered by having the upper part, the lower part, and the outer sides in the radial direction of the holder 602 as open ends.

Figure 10:
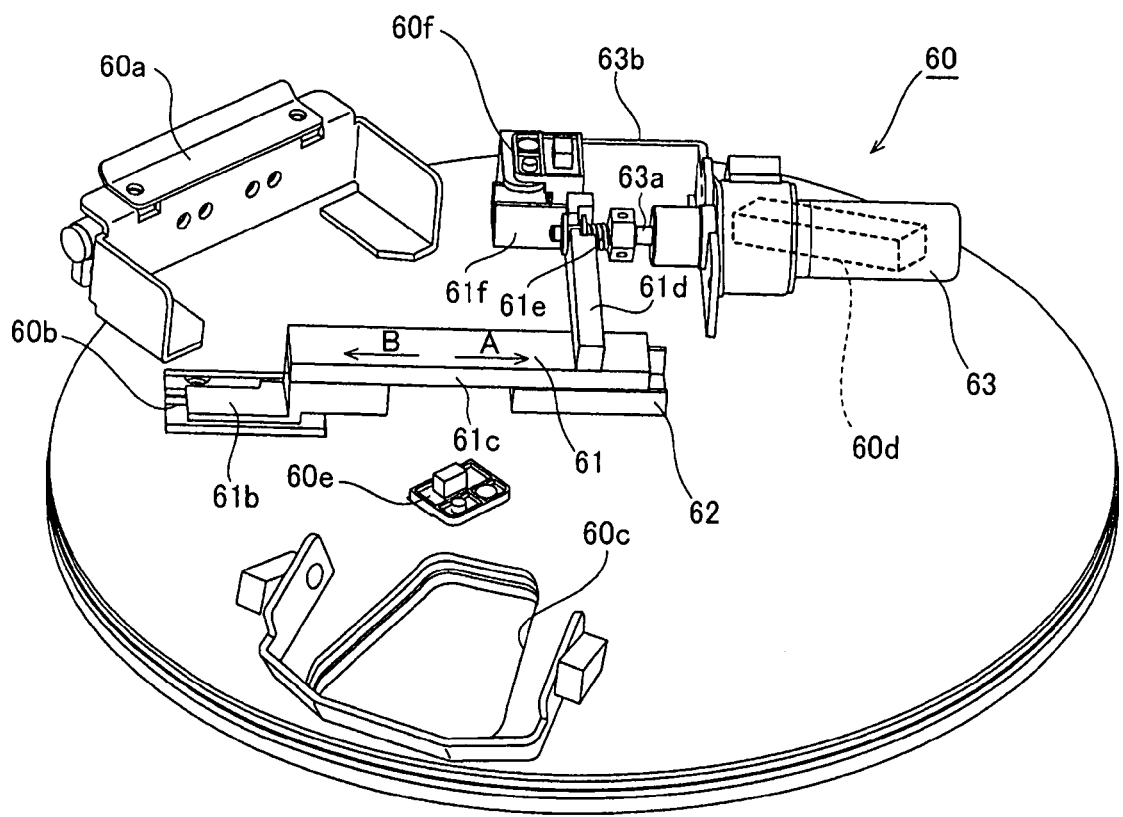
FIG. 10 is a perspective view showing a surface of the lid of the reagent installing unit shown in FIG. 6.
Figure 11:
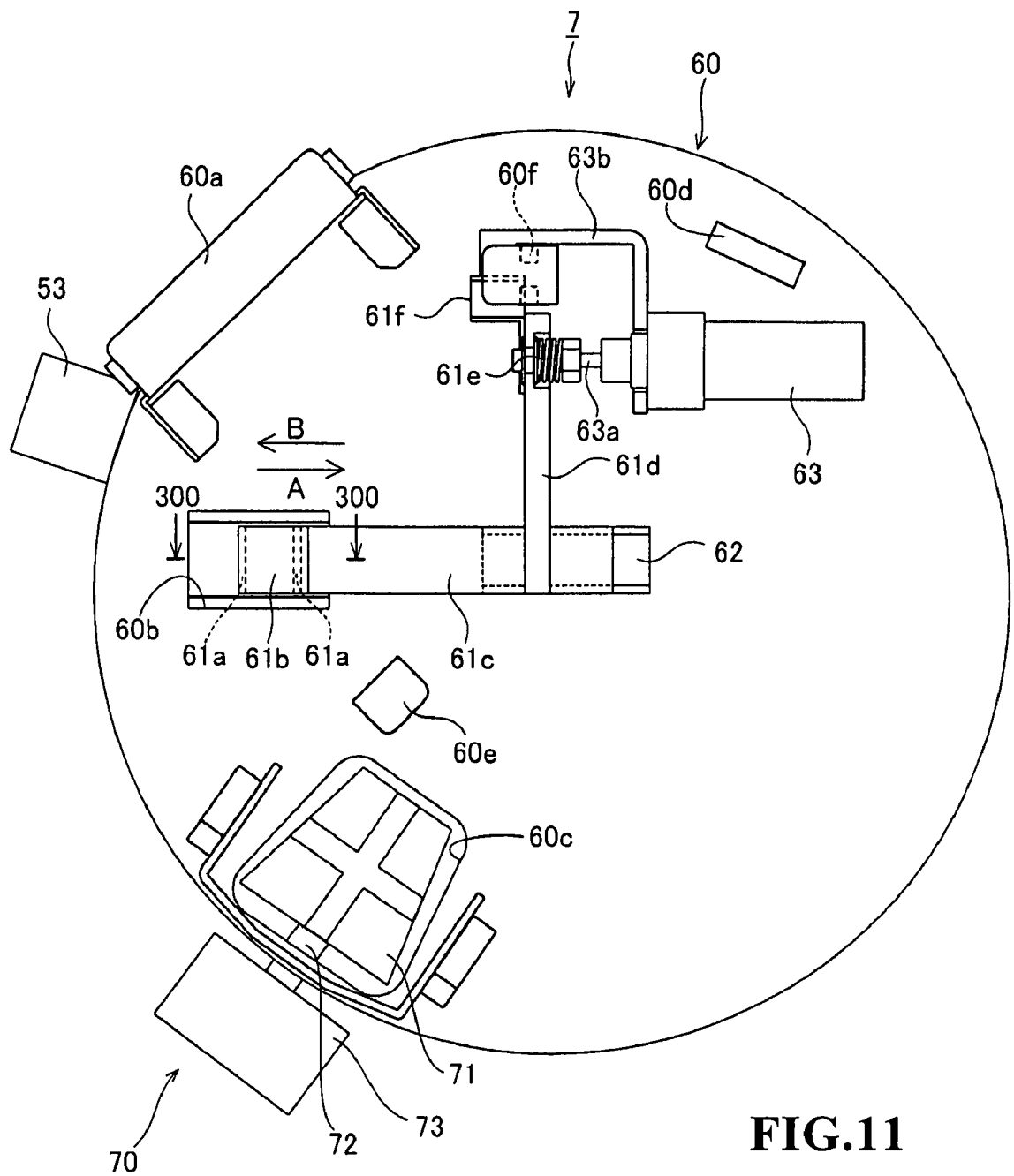
FIG. 11 is a plan view showing a surface of the lid of the reagent installing unit shown in FIG. 6.

As shown in FIG. 6, the lid 60 is attached in an openable and closable manner to the reagent holder 50 by way of a hinge part 60a. The lid 60 is configured to shield outside air so that the temperature in the reagent installing unit 7 is maintained at a low temperature (15° C.), and so as to enable the reagent in the reagent installing unit 7 to be suctioned from the outside and the reagent-containing assembly 300 to be placed in or taken out from the reagent installing unit 7. Specifically, as shown in FIGS. 10 and 11, the lid 60 has the hole 60b to be inserted with a pipette 9e of the reagent dispensing arm 9 when suctioning the reagent from the reagent container 310 (see FIG. 14) of the reagent-containing assembly 300, and the input/output hole 60c for placing in or taking out the reagent-containing assembly 300 from the reagent installing unit 7 by the raising and lowering unit 70. The size and the shape of the input/output hole 60c correspond to the planar shape of the reagent-containing assembly 300, and is formed so that one reagent-containing assembly 300 can pass therethrough. Furthermore, the lid 60 includes an openable/closable member 61 for opening or closing a slide lid 330 (see FIG. 14) of the reagent-containing assembly 300 arranged below the hole 60b, a linear movement guide 62 for slidably supporting the openable/closable member 61 in a substantially horizontal direction, and a stepping motor 63 for linearly driving the openable/closable member 61 in a reciprocating manner. The lid 60 is arranged with a reflection sensor 60d for detecting whether or not the reagent-containing assembly 300 is held in the holder 602 of the rack 600, a transmissive origin detection sensor 60e for detecting an origin position of the rack 600, and a transmissive sensor 60f for detecting an origin position of the openable/closable member 61. The sensor 60d is arranged on the front surface side of the lid 60 so that light can be irradiated towards the back surface side of the lid 60, and the origin detection sensor 60e is arranged on the back surface side of the lid 60. The transmissive sensor 60f is arranged on the front surface side of the lid 60.

Figure 12:
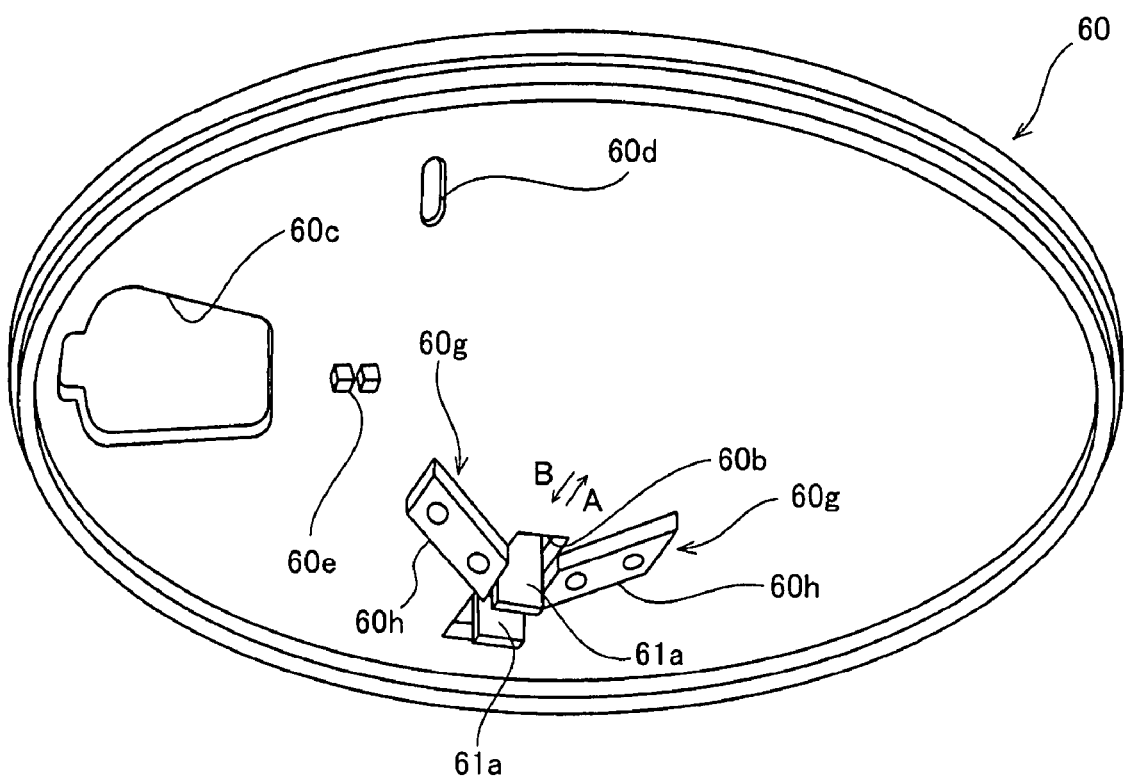
FIG. 12 is a perspective view showing a back surface of a lid of the reagent installing unit shown in FIG. 6.

As shown in FIG. 12, the openable/closable member 61 includes a two-forked engagement strip 61a that projects towards the lower side of the hole 60b. Furthermore, as shown in FIGS. 10 and 11, the engagement strip 61a is configured to linearly move in a reciprocating manner in the direction of the arrow A and the direction of the arrow B by way of coupling members 61b, 61c and 61d fixed to each other by the driving force of the stepping motor 63. The coupling member 61c is attached to the linear movement guide 62. The coupling member 61d is connected to a shaft 63a, which moves by the driving force of the stepping motor 63. A spring member 61e is arranged at a connecting portion of the coupling member 61d and the shaft 63a. The load on an engagement strip 333 (see FIG. 14) of the slide lid 330 that generates when the engagement strip 61a contacts is absorbed when closing the slide lid 330 with the engagement strip 61a (when the engagement strip 61a moves in the direction of the arrow B), as described above, due to elasticity of the spring member 61e. A detection strip 61f is attached to the coupling member 61d. When the detection strip 61f is detected by the sensor 60f, the openable/closable member 61 (engagement strip 61a) is positioned at the origin position (waiting position). The stepping motor 63 and the sensor 60f are fixed to a motor bracket 63b arranged on the surface of the lid 60.

Figure 13:
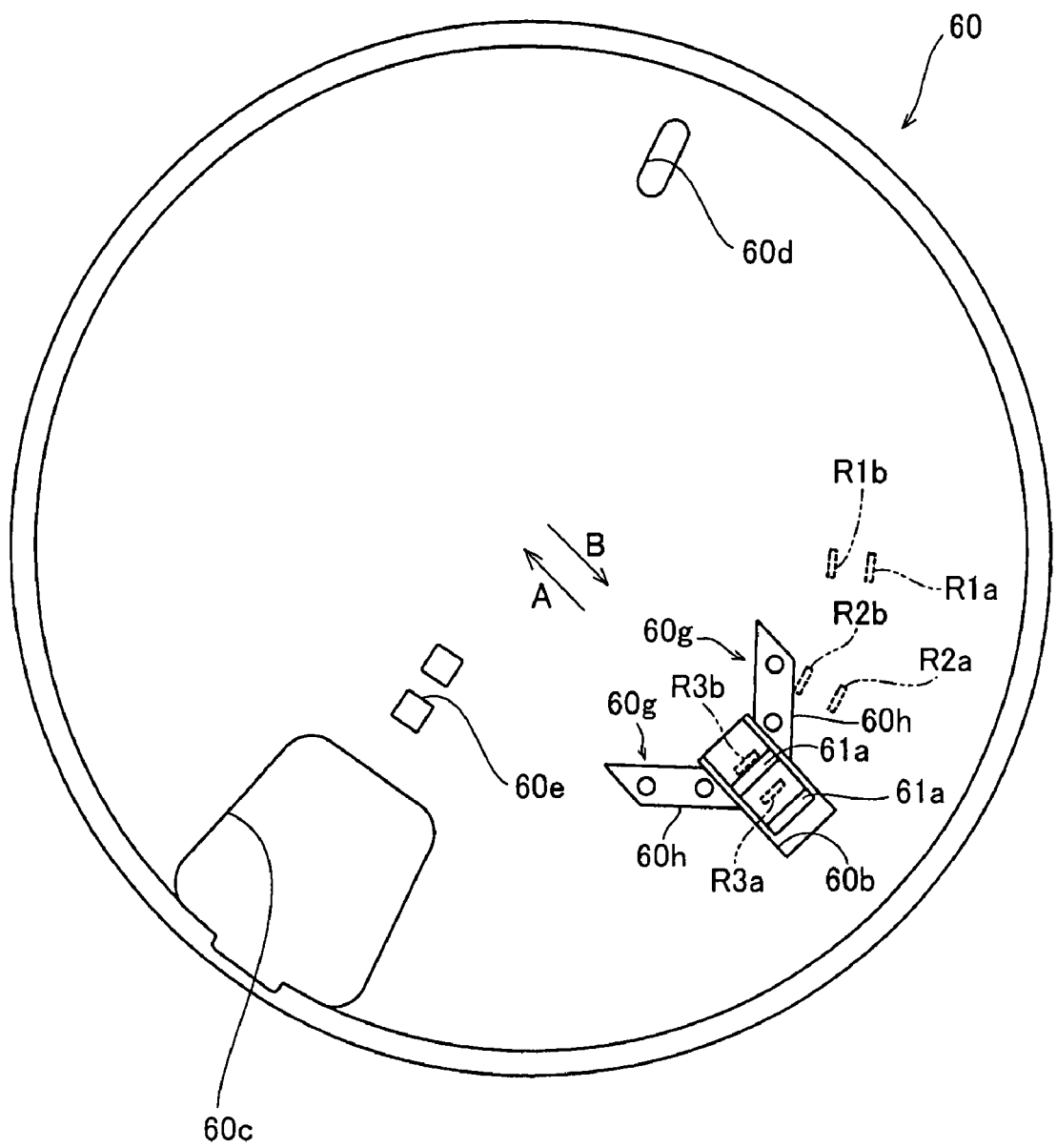
FIG. 13 is a plan view showing a back surface of the lid of the reagent installing unit shown in FIG. 6.
Figure 14:
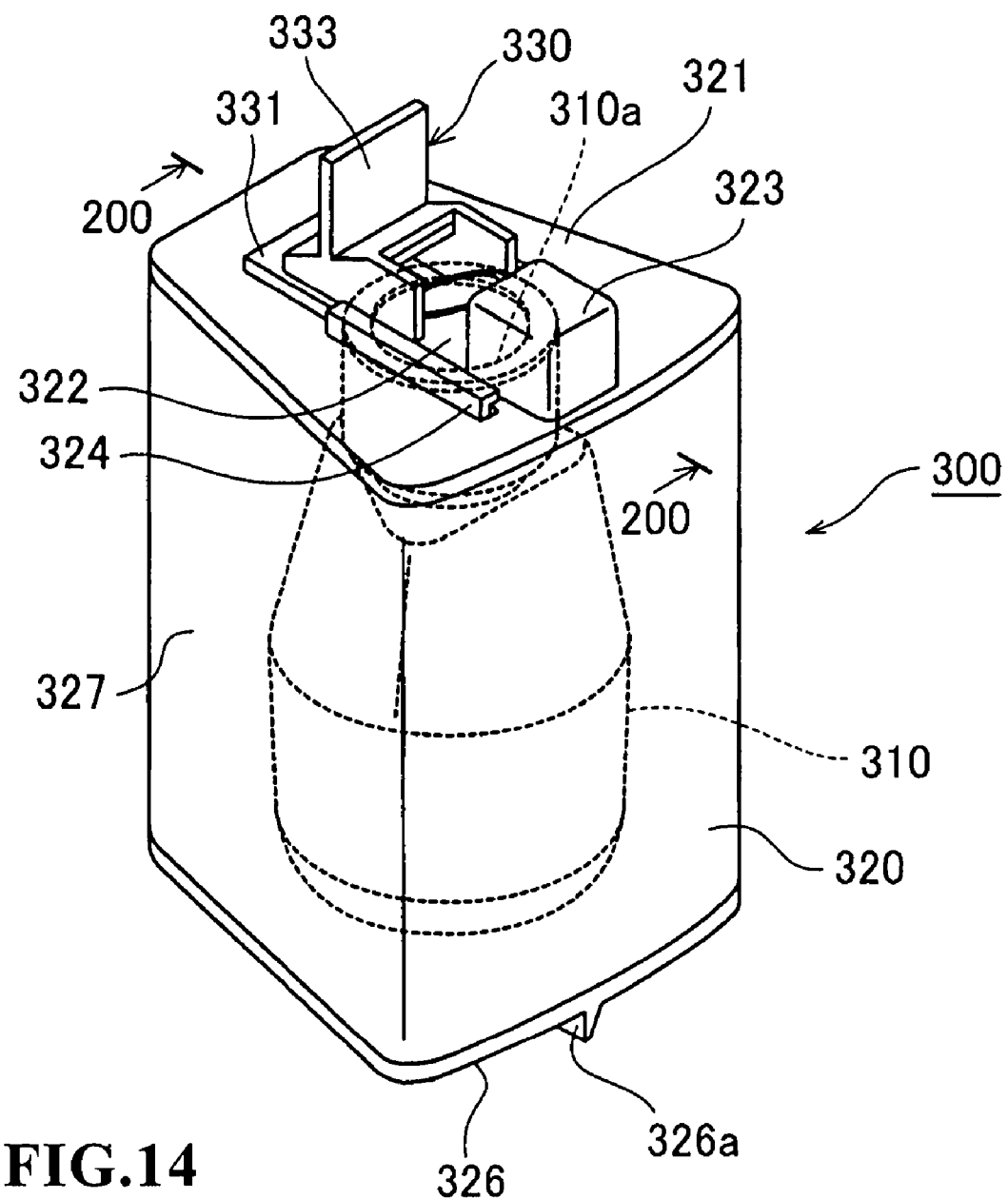
FIG. 14 is an outer appearance view of the reagent-containing assembly used in the immune analyzer according to one embodiment of the present invention.

When the reagent-containing assembly 300 is arranged below the hole 60b with the slide lid 330 closed, the engagement strip 333 (see FIG. 14) of the slide lid 330 of the reagent-containing assembly 300 is positioned between the two-forked engagement strips 61a of the openable/closable member 61. That is, as shown in FIG. 13, the engagement strip 333 of the slide lid 330 is configured to pass through the path of R1a, R2a, and R3a with the rotation of the rack 600 while the slide lid 330 is in the closed state. A pair of guide strips 60g is attached near the hole 60b of the back surface of the lid 60. The pair of guide strips 60g has a function of positioning the engagement strip 333 of the slide lid 330 between the two-forked engagement strips 61a of the openable/closable member 61 since the contacting surface 60h contacts and guides the engagement strip 333 of the slide lid 330 when the reagent-containing assembly 300 is arranged below the hole 60b with the slide lid 330 opened. That is, the engagement strip 333 of the slide lid 330 is configured to pass through the path of R1b, R2b, and R3a and not positioned at R3b with the rotation of the rack 600 while the slide lid 330 is opened.

The reflection sensor 60d is configured to detect whether or not the reagent-containing assembly 300 is held in the holder 602 of the rack 600. The transmissive origin detection sensor 30e has a function of detecting the origin detection strip 603 arranged in the rack 600 to detect the origin position of the rotating rack 600.

The raising and lowering unit 70 is arranged to place in or take out the reagent-containing assembly 300 with respect to the reagent installing unit 7. As shown in FIGS. 7 and 8, the raising and lowering unit 70 includes the mounting platform 71 on which the reagent-containing assembly 300 is mounted, an arm 72 for supporting the mounting platform 71, and a driving section 73 for sliding the arm 72 in the up and down direction. A groove 71a capable of engaging with a rib 326a formed at the bottom 326 of the case 320 of the reagent-containing assembly 300 is formed in the mounting platform 71. The arm 72 has a function of moving the mounting platform 71 in the up and down direction by the driving force of the driving section 73 arranged exterior to the reagent holder 50 by way of a hole (not shown) arranged in an outer wall part 51 and extending in the up and down direction. The raising and lowering unit 70 can hold the reagent-containing assembly 300 in the rack 600 by lowering the mounting platform 71 with the reagent-containing assembly 300 mounted on the mounting platform 71. The reagent-containing assembly 300 held by the rack 600 is lifted by moving the mounting platform 71 from the bottom to the top of the reagent-containing assembly 300 held by the rack 600, so that the reagent-containing assembly 300 can be taken out from the input/output hole 60c of the lid 60.

The configuration of the reagent-containing assembly 300 used in the immune analyzer 1 according to the present embodiment will now be described with reference to FIGS. 14 to 17.

Figure 15:
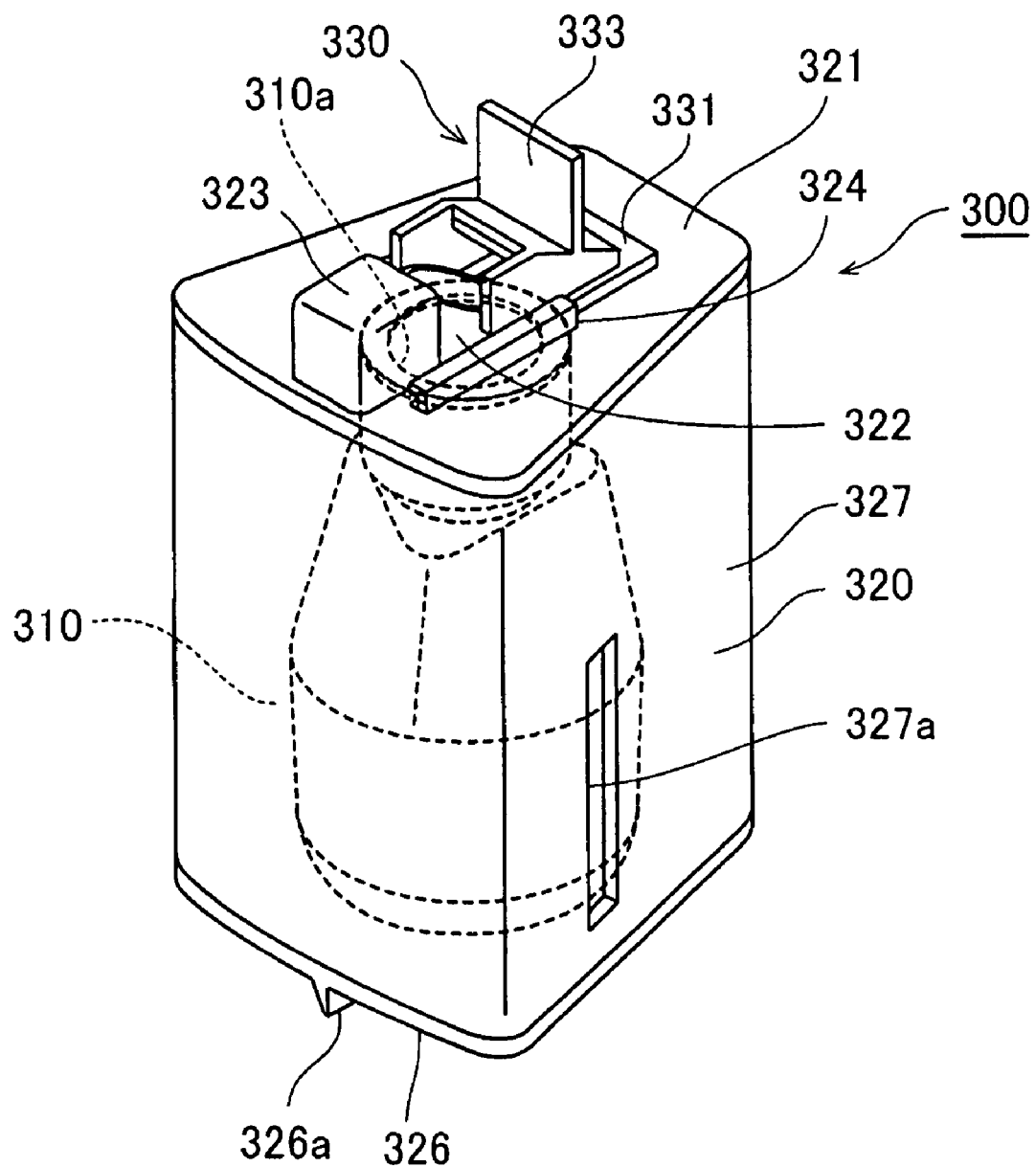
FIG. 15 is an outer appearance view of the reagent-containing assembly used in the immune analyzer according to one embodiment of the present invention.

As shown in FIGS. 14 to 17, the reagent-containing assembly 300 includes a reagent container 310 accommodating the R2 reagent, and a case 320 for accommodating the reagent container 310. A tubular part 322 inserted into the opening 310*a* of the reagent container 310, a reflection part 323 for reflecting the light irradiated by the reflection sensor 60*e* arranged on the lid 60, a slide rail 324 for sliding the slide lid 330, to be hereinafter described, and a concave part 325 for regulating the respective position of the slide lid 330 are arranged on the upper surface 321 of the case 320. Furthermore, the slid lid 330 that can seal the tubular part 322 is attached to the upper surface 321 of the case 320. The rib 326*a* that engages with the groove 71*a* of the mounting platform 71 of the raising and lowering unit 70 is arranged at the bottom surface 326 of the case 320. As shown in FIG. 15, a slit 327*a* for viewing the amount of reagent accommodated in the reagent container 310 is formed on the side surface 327 of the case 320.

Figure 16:
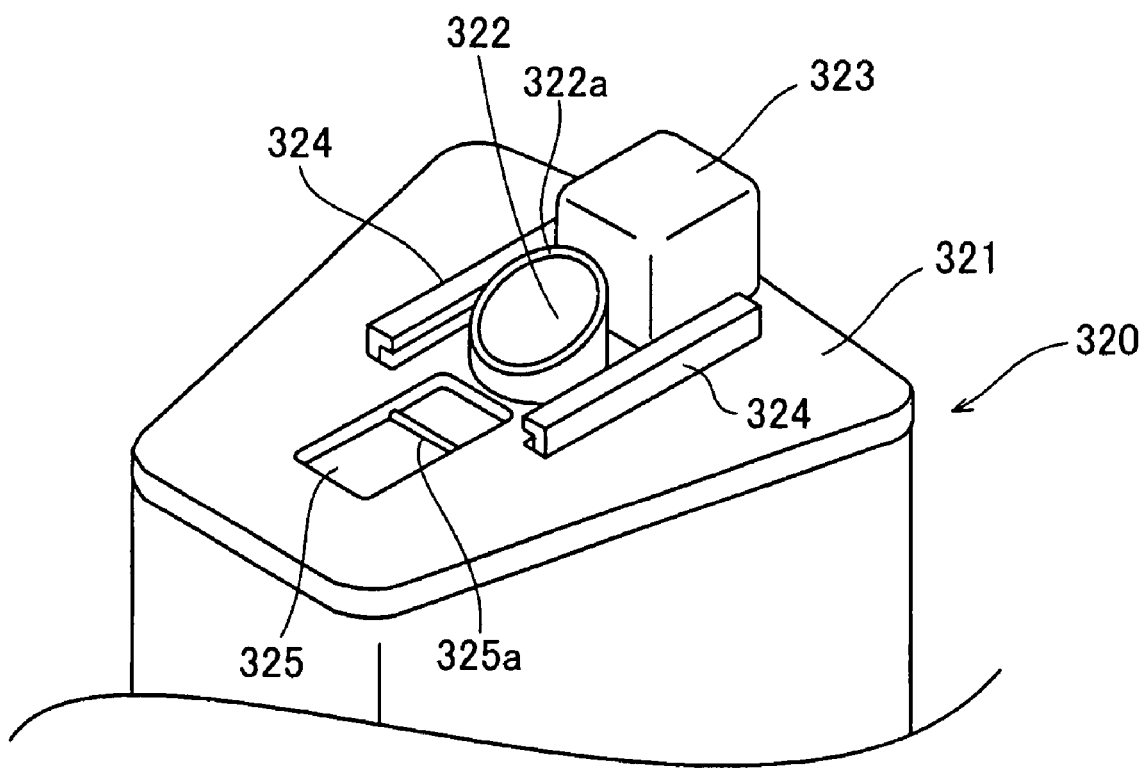
FIG. 16 is a perspective view showing an upper surface of the reagent-containing assembly used in the immune analyzer according to one embodiment.
Figure 17:
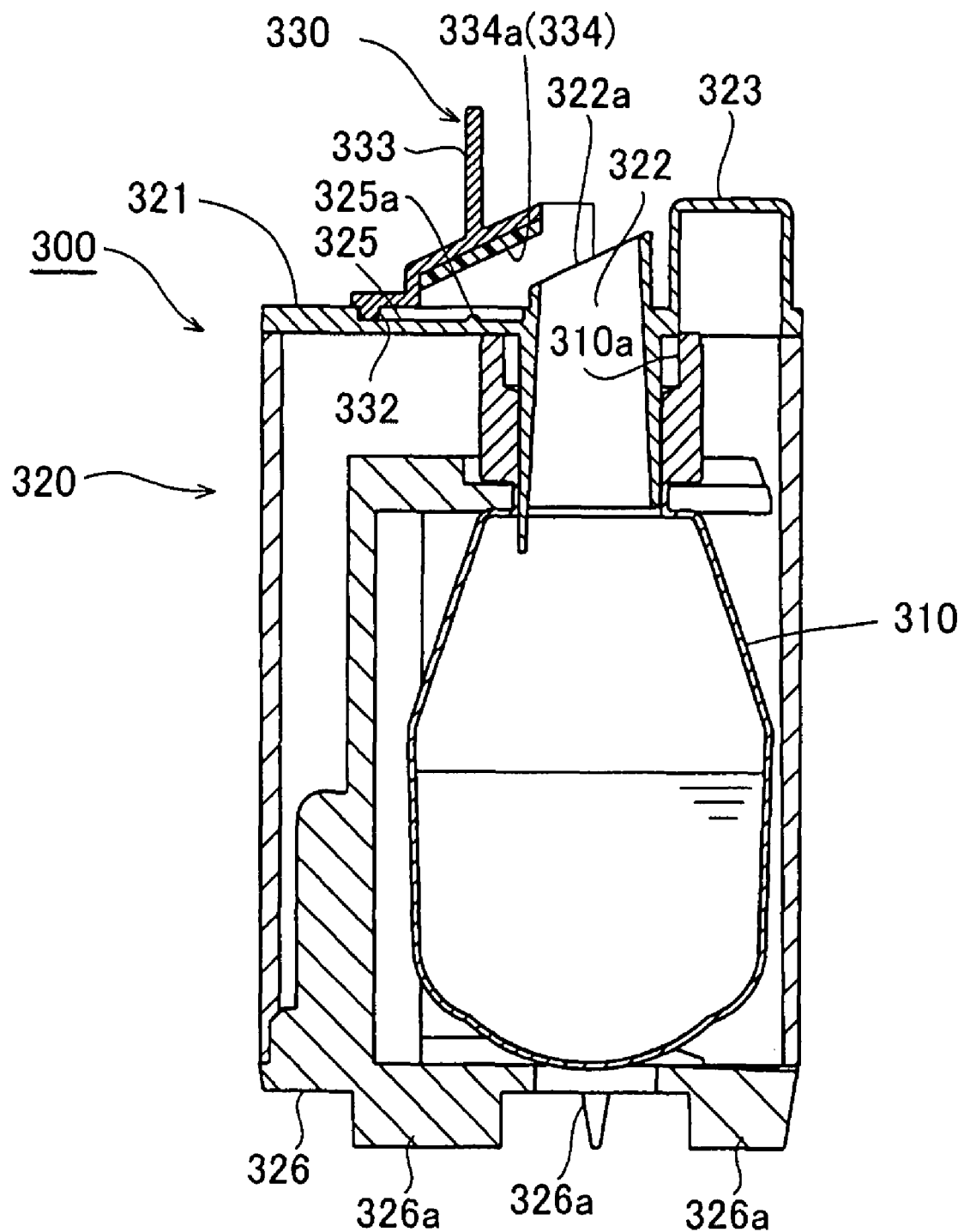
FIG. 17 is a cross sectional view taken along line 200-200 of FIG. 14.

As shown in FIGS. 16 and 17, the tubular part 322 is formed so that an opening end face 322*a* on the upper side has an inclined surface inclined by a predetermined angle from a horizontal surface. The concave part 325 has a function of regulating the movement of the slide lid 330 by contacting a projecting part 332 of the slide lid 330 to be hereinafter described, and suppressing the slide lid 330 from slipping off from the case 320. A convex shaped rib 325*a* that engages the projecting part 332 of the slide lid 330 when the slide lid 330 is at the position of closing the opening end face 322*a* on the upper side of the tubular part 322 is formed in the concave part 325. The slide lid 330 then can be fixed with the slide lid 330 sealing the tubular part 322.

The slide lid 330 is configured to open and close the tubular part 322 by sliding with respect to the case 320. The slide lid 330 includes an engagement part 331 (see FIG. 14) that engages the slide rail 324, the projecting part 332 (see FIG. 17) fitted into the concave part 325 of the upper surface 321, the engagement strip 333 that engages the openable/closable member 61 (engagement strip 61*a*) of the lid 60, and a contacting part 334 (see FIG. 17) formed to have an inclined surface inclined by a predetermined angle. As shown in FIG. 17, a plate shaped silicon sheet 334*a* that closely attaches to the opening end face 322*a* on the upper side of the tubular part 322 when the slide lid 330 seals the tubular part 322 is attached to the contacting part 334.

The angle of inclination of the opening end face 322*a* on the upper side of the tubular part 322 and the angle of inclination of the contacting part 334 of the slide lid 330 are substantially equal. The opening end face 322*a* and the silicon sheet 334*a* closely attach when the slide lid 330 slides in a direction from the lower side to the higher side of the opening end face 322*a* of the tubular part 322, whereby the reagent accommodated in the reagent container 310 is sealed.

The suctioning operation of suctioning the reagent from the reagent-containing assembly 300 in the immune analyzer 1 according to the present embodiment with the pipette 9*e* of the reagent dispensing arm 9 will now be described with reference to FIGS. 1, 8, 11, 13, and FIGS. 18 to 22.

Figure 18:
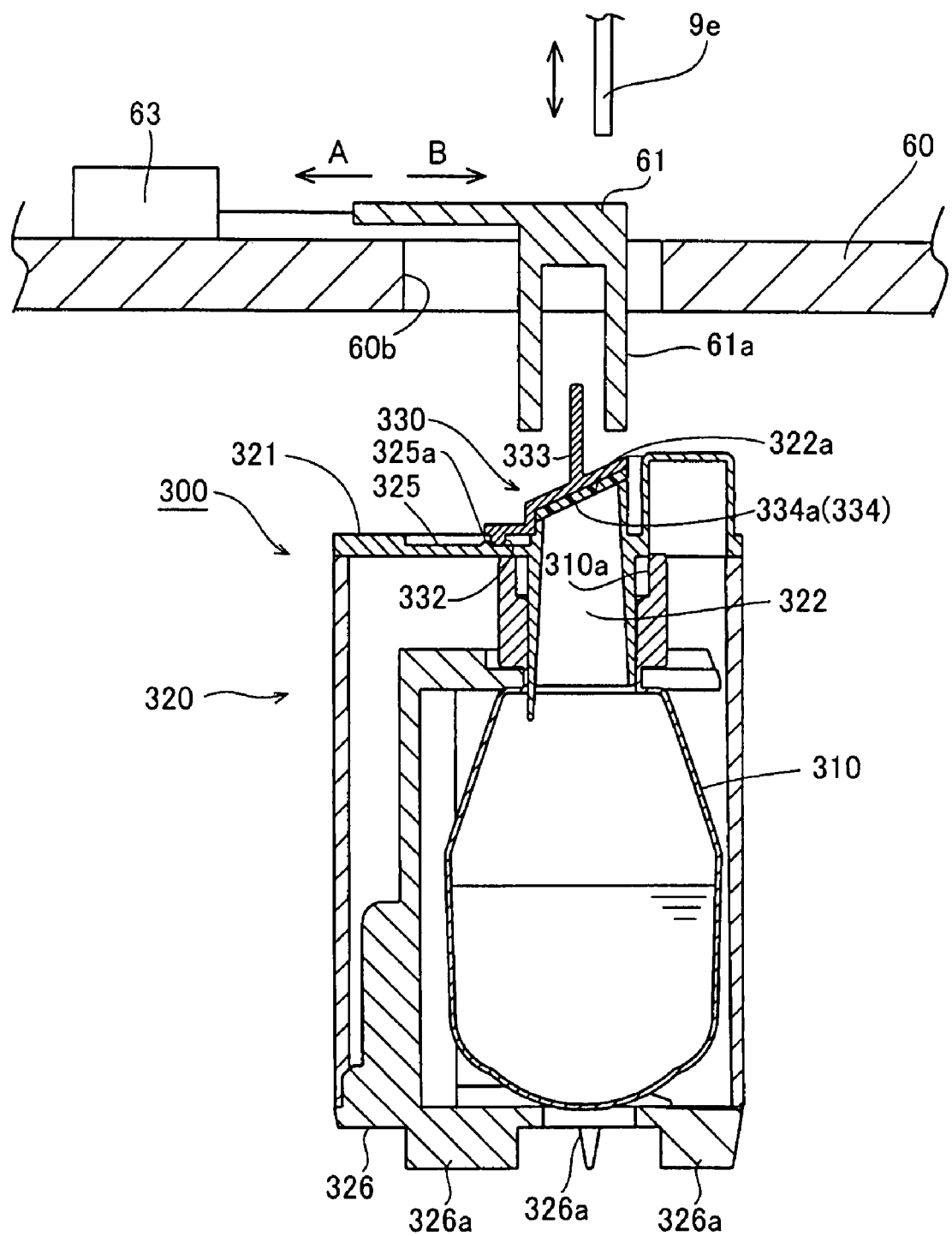
FIG. 18 is a cross sectional view taken along line 300-300 of FIG. 19.

As shown in FIG. 11, the openable/closable member 61 (engagement strip 61*a*) waits at the origin position (waiting position) at the start of the reagent suctioning operation. First, the reagent-containing assembly 300 including the reagent container 310 accommodating the reagent to be suctioned is moved to below the hole 60*b* of the lid 60 as the rotation shaft 52 (see FIG. 8) of the reagent holder 50 rotates the rack 600 holding the reagent-containing assembly 300. When the reagent-containing assembly 300 moves to below the hole 60*b* of the lid 60, the engagement strip 333 of the slide lid 330 is passed through the path of R1a, R2a, and R3a of FIG. 13 so as to be arranged between the two-forked engagement portions 61*a* of the openable/closable member 61 at the origin position if the slide lid 330 of the reagent-containing assembly 300 is closed, as shown in FIG. 18. When the reagent-containing assembly 300 moves to below the hole 60*b* of the lid 60, the engagement strip 333 of the slide lid 330 is guided by a guide strip 60*g* (see FIG. 13) arranged near the hole 60*b* of the lid 60 and passed through the path of R1b, R2b, and R3a of FIG. 13 so as to be arranged between the two-forked engagement portions 61*a* of the openable/closable member 61 at the origin position if the slide lid 330 of the reagent-containing assembly 300 is opened.

Figure 19:
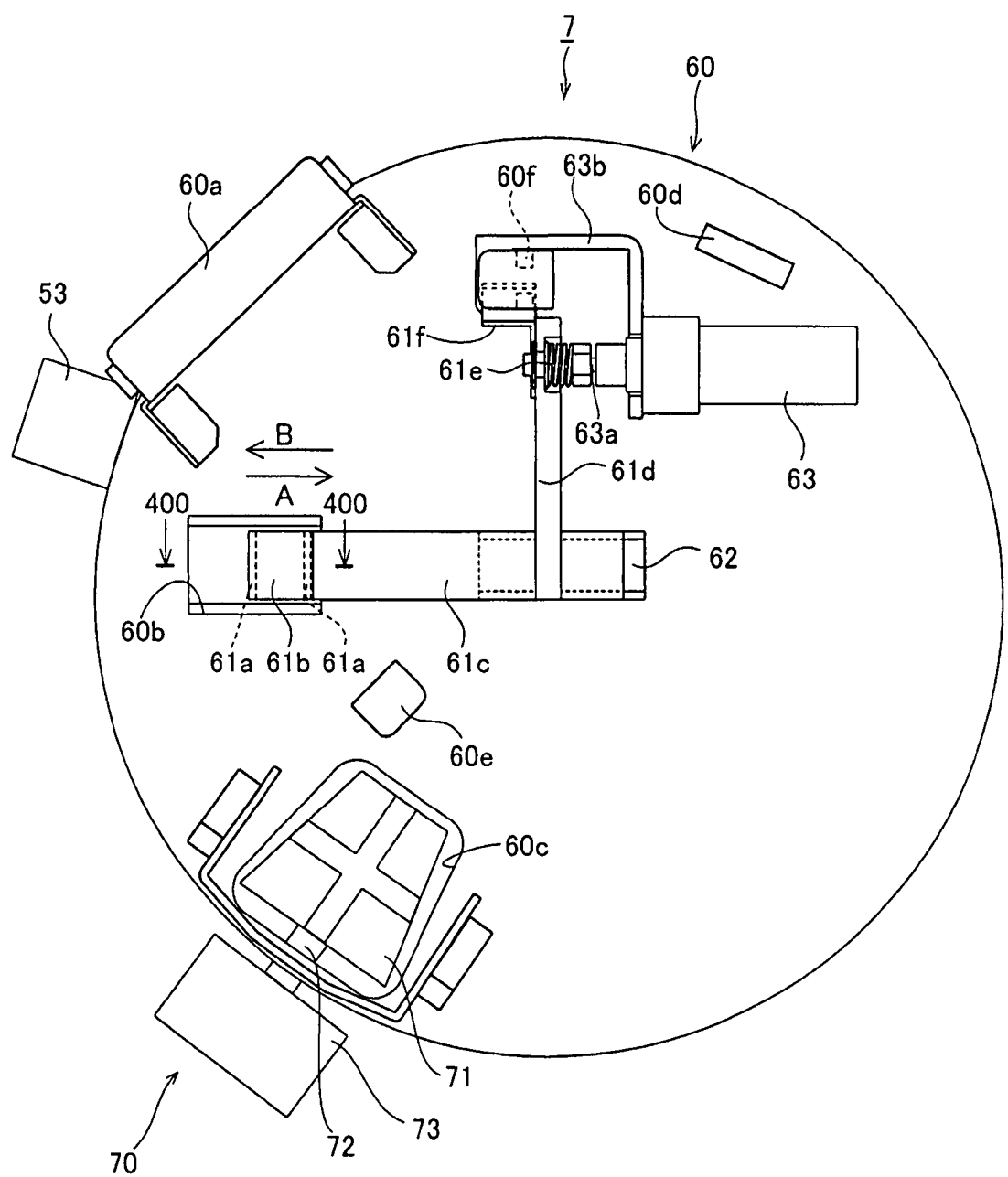
FIG. 19 is a plan view showing the lid of the slide lid in the opened state.
Figure 20:
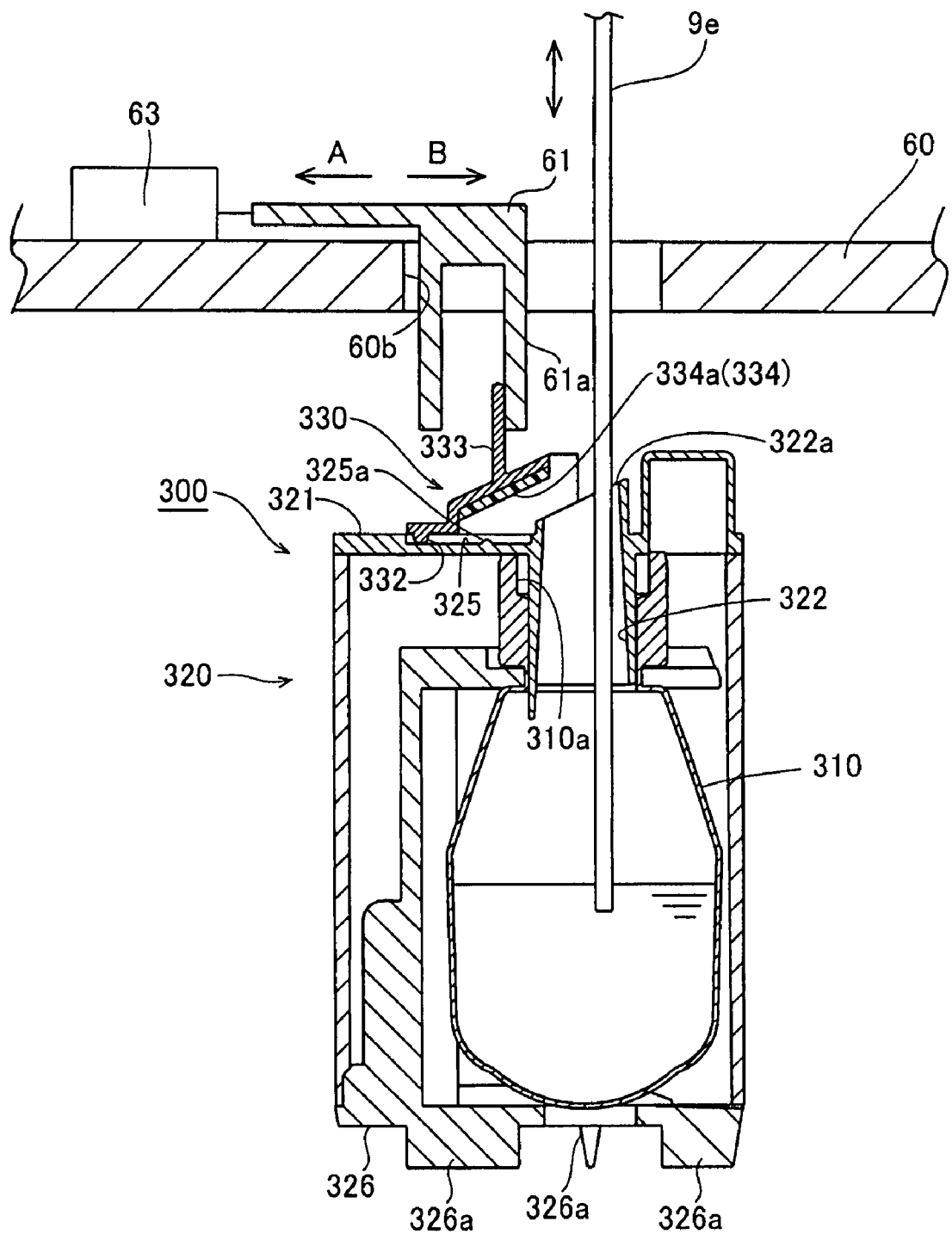
FIG. 20 is a cross sectional view taken along line 400-400 of FIG. 19.

First, the detecting function of the sensor 60*f* (see FIG. 11) for detecting the origin position of the openable/closable member 61 is turned OFF in this state. As shown in FIG. 19, the openable/closable member 61 is sled in the direction of the arrow E by the stepping motor 63. Thus, as shown in FIG. 20, the engagement strip 333 of the slide lid 330 is sled in the direction of the arrow E by the two-forked engagement portions 61*a*, whereby the slide lid 330 is in the opened state. The pipette 9*e* of the reagent dispensing arm 9 can be inserted into the reagent container 310 through the region opened when the openable/closable member 61 is sled of the hole 60*b* of the lid 60 and the tubular part 322. The pipette 9*e* can be moved to above the hole 60*b* of the lid 60 by the turning of the motor 9*a* and the drive transmitting part 9*b*. As shown in FIG. 20, the pipette 9*e* is inserted into the reagent container 310 through the hole 60*b* and the tubular part 322 as the pipette 9*e* is lowered with the slide lid 330 in the opened state, and the reagent is suctioned.

The pipette 9*e* that has suctioned the reagent is raised and turned by the motor 9*a* and the drive transmitting part 9*b*, and moved to the upper side of the primary reaction unit 11 (see FIG. 1). The reagent suctioned from the reagent container 310 is then dispensed into the cuvette 150 of the primary reaction unit 11.

Figure 21:
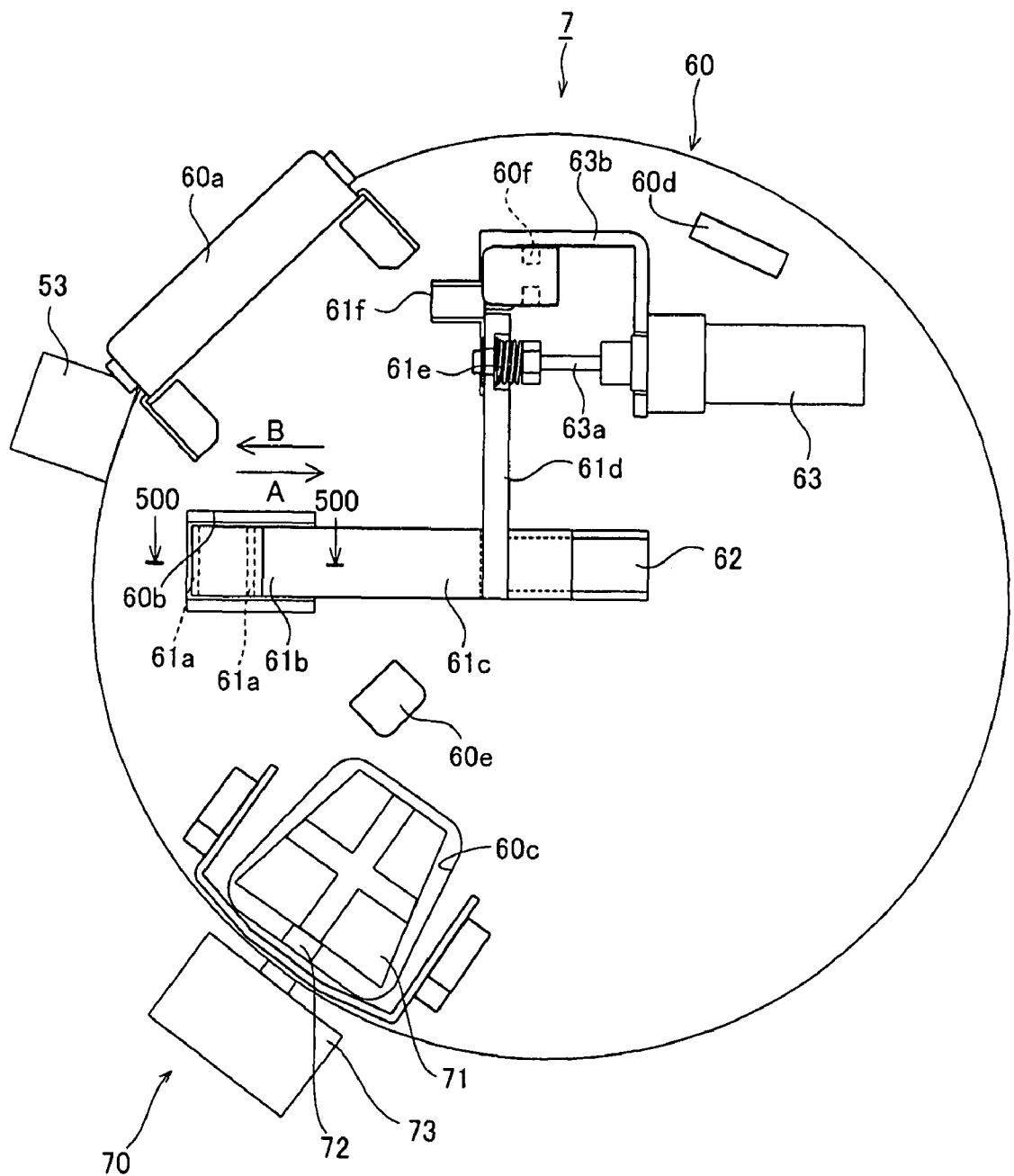
FIG. 21 is a plan view showing the lid of the slide lid in the closed state.
Figure 22:
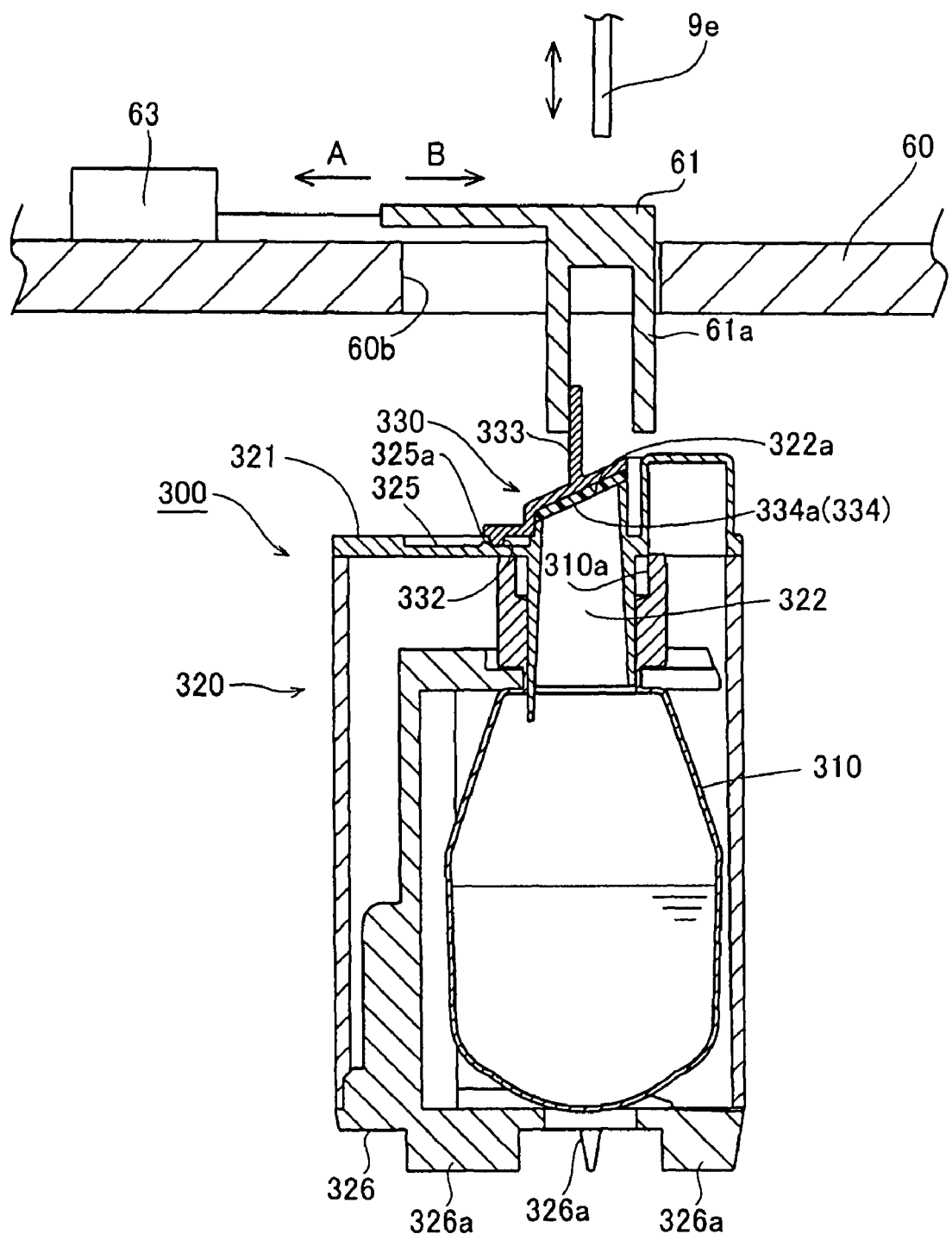
FIG. 22 is a cross sectional view taken along line 500-500 of FIG. 21.

As shown in FIG. 21, after the suctioning of the reagent is terminated, the openable/closable member 61 is moved in the direction of the arrow F by the stepping motor 63, whereby the engagement strip 333 of the slid lid 330 slides in the direction of the arrow F with the two-forked engagement portions 61*a*. The opening end face 322*a* on the upper side of the tubular part 322 and the silicon sheet 334*a* attached to the contacting part 334 of the slide lid 330 thereby closely attach to seal the reagent, as shown in FIG. 22. The projecting part 322 of the slide lid 330 and the rib 325*a* formed in the concave part 325 of the slide lid 330 engage with the opening end face 322*a* on the upper side of the tubular part 322 and the silicon sheet 334*a* closely attached, and the slide lid 330 is fixed to the case 320. The sealed state of the reagent is maintained even when the rack 600 is rotated and the reagent-containing assembly 300 is moved.

Subsequently, the detecting function of the sensor 60*f* for detecting the origin position of the openable/closable member 61 (engagement strip 61*a*) is turned ON. The openable/closable member 61 is moved in the direction of the arrow E until the detection strip 61*f* is detected by the sensor 60*f*. The openable/closable member 61 (engagement strip 61*a*) is then positioned at the origin position or the waiting position, as shown in FIGS. 11 and 18.

The configuration of the reagent installing unit 6 is similar to the configuration of the reagent installing unit 7 except that two opening/closing mechanisms of the lid member are arranged in the lid 30 in correspondence to the reagent-containing assembly including two reagent containers for the R1 reagent and for the R2 reagent, and thus the description thereof will be omitted. The operation of suctioning the reagent from the reagent-containing assembly installed in the reagent installing unit 6 is also similar to the above, and thus the description thereof will be omitted.

In the present embodiment, the slide lid 330 that opens/closes the opening 310a by being linearly moved in a reciprocating manner in a substantially horizontal direction is automatically opened/closed using the reagent-containing assembly 300 including the slide lid 330 of a simple configuration by linearly moving the openable/closable member 61 in a reciprocating manner in the horizontal direction, as described above.

Furthermore, in the present embodiment, the reagent dispensing arm 9 is configured to insert the pipette 9e into the reagent-containing assembly 300 through the hole 60b and the opening 310a when the openable/closable member 61 opens the slide lid 330 and to suction the reagent, as described above. The disadvantage in the user accidentally inserting his/her hand into the reagent holder 50 holding the reagent-containing assembly 300 is thereby prevented by the lid 60. The slide lid 330 of the reagent-containing assembly 300 can be opened/closed without opening the lid 60 of the reagent installing unit 7, and the reagent can be suctioned from the reagent-containing assembly 300.

Furthermore, in the present embodiment, the inside of the reagent installing unit 7 can be efficiently cooled since the inside of the reagent holder 50 covered with the lid 60 is cooled by cooling the inside of the reagent installing unit 7 with Peltier element, as described above.

In the present embodiment, the slide lid 330 can be opened/closed by linearly moving the engagement strip 61a in a reciprocating manner in the direction of the arrow A and in the direction of the arrow B by means of the stepping motor 63 with the engagement strip 61a of the openable/closable member 61 engaged to the engagement strip 333 of the slide lid 330 of the reagent-containing assembly 330, as described above.

In the present embodiment, the reagent-containing assembly 300 can be replaced without opening the lid 60, and furthermore, temperature rise in the reagent installing unit 7 can be suppressed by forming the input/output hole 60c having a size that allows one reagent-containing assembly 300 held by the reagent installing unit 7 to pass through in the lid 60, as described above.

In the present embodiment, the engagement strip 333 of the slide lid 330 is guided so as to engage with the engagement strip 61a of the openable/closable member 61 by the guide strip 60g arranged at the lower surface of the lid 60 when the reagent-containing assembly 300 is moved to below the hole 60b with the slide lid 330 opened, as described above, so that the slide lid 330 is reliably opened/closed by the openable/closable member 61.

In the present embodiment, the engagement strip 61a of the openable/closable member 61 and the engagement strip 333 of the slide lid 330 can be easily engaged by moving the reagent-containing assembly 300 to below the hole 60b by rotatably moving the reagent-containing assembly 300 held in the rack 600 in a substantially horizontal direction, as described above.

In the present embodiment, the opening end face 322a of the tubular part 322 can be sealed by linearly moving the slide lid 330 substantially horizontally in a direction from the lower side to the higher side of the opening end face 322a by forming the opening end face 322a of the tubular part 322 of the reagent-containing assembly 300 and the contacting part 334 of the slide lid 330 with substantially the same angle of inclination, as described above. Therefore, the friction that occurs between the contacting part 334 and the opening end face 322a of the tubular part 322 is reduced, and degradation by friction is prevented. Since friction is less likely to occur, the opening end face 322a of the tubular part 322 can be closed with a small force. The slide lid 330 thus does not need to be opened/closed by moving the openable/closable member 61 with a large driving force.

The embodiments disclosed herein are illustrative and should not be construed as being restrictive. The scope of the invention is defined by the appended claims rather than by the description of the embodiments, and all changes that fall within meets and bounds of the claims, or equivalence of such meets and bounds are therefore intended to be embraced by the claims.

An example of applying the present invention to the immune analyzer 1 has been described in the above embodiment, but the present invention is not limited thereto, and may be applied to biochemical analyzers and blood coagulation measurement devices.

Moreover, an example of forming the opening end face 322a on the upper side of the tubular part of the reagent-containing assembly 300 as an inclined surface inclined by a predetermined angle has been described in the above embodiment, but the present invention is not limited thereto, and the opening end face on the upper side of the tubular part may be formed as a horizontal surface.

In the present embodiment, the reagent-containing assembly 300 has the reagent container 310 accommodated in the case 320, and the R2 reagent is accommodated in the reagent container 310, but the reagent container 310 does not need to be accommodated in the case 320, and the reagent container 310 itself may be the reagent-containing assembly.

What is claimed is:

1. An analyzer comprising:
    an assembly holder for holding a reagent-containing assembly comprising an opening and a lid member for opening and closing the opening;
    an opening-closing section for opening and closing the opening by linearly moving the lid member in a reciprocating manner to substantially horizontal directions;
    a reagent suctioning section for suctioning reagent by inserting a pipette into the reagent-containing assembly through the opening; and
    an analyzing section for analyzing an analyzing specimen comprising a sample and the reagent.

2. The analyzer according to claim 1, wherein
    the assembly holder comprises a holder lid of the assembly holder having a pipette inserting port in which the pipette is inserted;
    the opening-closing section is arranged on the holder lid; and
    the reagent suctioning section inserts the pipette into the reagent-containing assembly through the pipette inserting port and the opening.

3. The analyzer according to claim 2, further comprising a cooling section for cooling the inside of the assembly holder.

4. The analyzer according to claim 2, wherein the opening-closing section comprises,
    an engagement part configured for engaging with the lid member of the reagent-containing assembly through the pipette inserting port; and
    a driving section, arranged on an upper surface of the holder lid, for linearly moving the engagement part in a reciprocating manner to the substantially horizontal directions.

5. The analyzer according to claim 2, wherein the holder lid has an assembly hole having a size for passing one reagent-containing assembly held by the assembly holder.

6. The analyzer according to claim 4, further comprising
an assembly moving section for moving the reagent-containing assembly held by the assembly holder to a substantially horizontal direction; and
a guide section, arranged on the lower surface of the holder lid, for guiding so that the lid member engages the engagement part by contacting the lid member with the movement of the reagent-containing assembly by the assembly moving section.

7. The analyzer according to claim 1, further comprising an assembly moving section for arranging the reagent-containing assembly at a position of opening and closing the opening by the opening-closing section by moving the reagent-containing assembly held by the assembly holder to a substantially horizontal direction.

8. The analyzer according to claim 1, wherein
a surface including an edge of the opening of the reagent-containing assembly is inclined from a horizontal surface;
the lid member has a closing surface having an inclination of substantially the same as an inclination of the surface including the edge of the opening; and
the closing surface closes the opening by linearly moving to one of the substantially horizontal directions, wherein the direction is a direction from the lower side to the higher side of the closing surface.

9. A reagent-containing assembly comprising:
an opening; and
a lid member for opening and closing the opening by linearly moving in a reciprocating manner to substantially horizontal directions; wherein
a surface including an edge of the opening is inclined from a horizontal surface;
the lid member comprises a closing surface having an inclination of substantially the same as the inclination of the surface including the edge of the opening; and
the closing surface closes the opening by linearly moves to one of the substantially horizontal directions, wherein the direction is a direction from the lower side to the higher side of the closing surface.

10. The reagent-containing assembly according to claim 9, further comprising a slide rail for guiding the lid member so as to linearly move to the substantially horizontal directions.

11. The reagent-containing assembly according to claim 9, wherein the lid member further comprises an engagement strip projected upward for engaging an engagement part that linearly moves to the substantially horizontal directions.

12. The reagent-containing assembly according to claim 9, wherein the reagent-containing assembly comprises a reagent container, a reagent container holder for holding the reagent container, and a cover, attached to the reagent container holder, for covering the reagent container.

13. The reagent-containing assembly according to claim 12, wherein the opening is formed in the reagent container and the lid member is arranged on the cover.

14. The reagent-containing assembly according to claim 9, further comprising reagent contained in the reagent-containing assembly.

15. The reagent-containing assembly according to claim 14, wherein the reagent is reagent used in immune measurement.

16. A reagent suctioning method for suctioning reagent contained in a reagent-containing assembly comprising an opening and a lid member for opening and closing the opening by linearly moving in a reciprocating manner in substantially horizontal directions; the method comprising the steps of:
opening the opening by linearly moving the lid member in a first substantially horizontal direction;
suctioning the reagent contained in the reagent-containing assembly through the opened opening; and
closing the opening by linearly moving the lid member in a second substantially horizontal direction opposite the first direction.

17. The reagent suctioning method according to claim 16, further comprising an assembly moving step of arranging the reagent-containing assembly at a suction position of the reagent by horizontally moving the reagent-containing assembly prior to the opening step.

18. The reagent suctioning method according to claim 17, wherein the assembly moving step further comprises a preliminary closing step of closing the opening by linearly moving the lid member in the second substantially horizontal direction when the lid member is opened in the assembly moving step.

19. The reagent suctioning method according to claim 18, wherein the closing of the opening in the preliminary closing step is executed with horizontal movement of the reagent-containing assembly.

20. The reagent suctioning method according to claim 16, wherein the closing step further comprises a fixing step of fixing the lid member at a position at which the opening is closed.

* * * * *